US008415305B2

(12) United States Patent
Krastel et al.

(10) Patent No.: US 8,415,305 B2
(45) Date of Patent: *Apr. 9, 2013

(54) USE OF CYCLIC DEPSIPEPTIDES TO INHIBIT KALLIKREIN 7

(75) Inventors: Philipp Krastel, Basel (CH); Brigitta-Maria Liechty, Basel (CH); Esther Schmitt, Basel (CH); Erwin Paul Schreiner, Vienna (AT)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/673,785

(22) PCT Filed: Aug. 14, 2008

(86) PCT No.: PCT/EP2008/060693
§ 371 (c)(1),
(2), (4) Date: Feb. 17, 2010

(87) PCT Pub. No.: WO2009/024528
PCT Pub. Date: Feb. 26, 2009

(65) Prior Publication Data
US 2011/0092437 A1     Apr. 21, 2011

(30) Foreign Application Priority Data

Aug. 17, 2007  (EP) .................................... 07114505

(51) Int. Cl.
*A61K 38/12* (2006.01)
*C07K 7/54* (2006.01)
*A61P 17/00* (2006.01)
*A61P 17/06* (2006.01)
*A61P 17/04* (2006.01)

(52) U.S. Cl. ........................ 514/20.1; 514/20.3; 530/317
(58) Field of Classification Search ........................ None
See application file for complete search history.

(56) References Cited

U.S. PATENT DOCUMENTS 5,595,756 A * 1/1997 Bally et al. .................... 424/450
2012/0196790 A1   8/2012 Krastel et al.

FOREIGN PATENT DOCUMENTS

| WO | 95/34558 A1 | 12/1995 |
| WO | 2004/108139 A | 12/2004 |
| WO | 2005/075667 A | 8/2005 |
| WO | 2009024527 A1 | 2/2009 |

OTHER PUBLICATIONS

Definition of derivative from http://cancerweb.ncl.ac.uk/omd/about. html, pp. 1-5. Accessed Jul. 7, 2005.*
Definition of residue from http//dictionary.reference.com/browse/residue, pp. 1-4. Accessed Jul. 13, 2009.*
Rudinger J, "Characteristics of the amino acids as components of a peptide hormone sequence," Peptide Hormones, JA Parsons Edition, University Park Press, Jun. 1976, pp. 1-7.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Sporn MB, Suh N, "Chemoprevention of cancer," Carcinogenesis, 2000, 21(3): 525-530.*
Auerbach R, Akhtar N, Lewis RL, Shinners, BL, "Angiogenesis assays: Problems and pitfalls," Cancer and Metastais Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Cancer Drug Design and Discovery Neidle, Stephen, ed. (Elsevier/Academic Press, 2008) pp. 427-431.*
"Designing Custom Peptides," from SIGMA Genosys, pp. 1-2. Accessed Dec. 16, 2004.*
Harada Ken-ichi et al., "Co-production of Microcystins and Aeruginopeptins by Natural Cyanobacterial Bloom"; Environ Toxicol 16(4):298-305 (2001).
von Elert Eric, et al., "Cyanopeptolin 954, a Chlorine-Containing Chymotrypsin Inhibitor of *Microcystis aeruginosa* NIVA Cya 43", J. Nat. Prod. 68(9):1324-1327 (Sep. 2005).
Itou Yusai et al., "Oscillapeptins A to F, Serine Protease Inhibitors from the Three Strains of *Oscillatoria agardhii*," Tetrahedron 55(22)6871-6882 (May 28, 1999).
McDonough, Michael et al., "New Structural Insights into the Inhibition of Serine Proteases by Cyclic Peptides from Bacteria," Chemistry & Biology 10(10):898-900 (Oct. 2003).
Franzke, Claus-W et al., "Antileukoprotease Inhibits Stratum Corneum Chymotryptic Enzyme Evidence for a Regulative Function in Desquamation," Journal of Biological Chemistry 271(36):21886-21890 (Sep. 6, 1996)
Banker R et al., "Inhibitors of Serine Proteases from a Waterbloom of the Cyanobacterium *Microcystis* sp," Tetrahedron 55(35):10835-10844 (Aug. 27, 1999).
Bonjouklian R et al., "A90720A, A Serine Protease Inhibitor Isolated From a Terrestrial Blue-Green Algae *Microchaete loktakensis*," Tetrahedron 52(2):395-404 (Jan. 8, 1996).
Reshef V et al., "Protease inhibitors from a water bloom of the cyanobacterium *Microcystis aeruginosa*," Tetrahedron 57(14):2885-2894 (Apr. 2, 2001)

(Continued)

*Primary Examiner* — Julie Ha
(74) *Attorney, Agent, or Firm* — Sophie Binet Cross

(57) ABSTRACT

The present application relates to cyclic depsipeptides of Formula I: or derivatives thereof, wherein X, $A_1$, $A_2$, $A_3$, $A_4$, $A_5$, $A_6$ and $A_7$ are defined herein. The cyclic depsipeptides of Formula I are inhibitors of kallikrein 7 and thus can be employed for the treatment of kallikrein-7 dependent diseases.

8 Claims, 8 Drawing Sheets

OTHER PUBLICATIONS

Fairlie D P et al., "Conformational Selection of Inhibitors and Substrates by Proteolytic Enzymes: Implications for Drug Design and Polypeptide Processing," J. Med. Chem. 43(7):1271-1281 (2000).

Matthew Susan et al., "Lyngbyastatin 4 a dolastatin 13 analogue with elastase and chymotrypsin inhibitory activity from the marine cyanobacterium *Lyngbya confervoides*," J. Nat. Prod. 70(1):124-127 (Jan. 2007).

Matsuda H., "Structures of serine protease inhibitors from freshwater blue-green algae," Tennen Yuki Kagobutsu Toronkai Koen Yoshishu 35:654-661 (1993).

Radau G., "Serine proteases inhibiting cyanopeptides," Pharmazie 55(8):555-560 (Aug. 2000).

Egeirud T., "Purification and preliminary Characterization of Stratum Corneum Chymotryptic Enzyme: A Proteinase that may be involved in desquamation," J. Invest. Dermatol. 101(2):200-204 (1993).

Grach-Pogrebinsky et al., "Protease Inhibitors from a Slovenian Lake Bled Toxic Waterbloom of the Cyanobacterium *Planktothrix Rubescens*," Tetrahedron 59:8329-8336 (2003).

Matern et al., "Binding Structure of Elastase Inhibitor Scyptolin A," Chemistry & Biology 10:997-1001 (Oct. 2003).

Nakanishi et al., "Structure of Porcine Pancreatic Elastase Complexed with FR901277, a Novel Macrocyclic Inhibitor of Elastases, at 1.6 A Resolution," Biopolymers 53(5):434-445 (2000).

Namikoshi et al., "Bioactive compounds produced by cyanobacteria," Journal of Industrial Microbiology 17:373-384 (1996).

Hiemstra, P.S., "Novel roles of protease inhibitors in infection and inflammation," Biochemical Society Transactions 30(2):116-120 (2002).

Kunze et al., "Chondramides A-D, New Antifungal and Cytostatic Depsipeptides from *Chondromyces crocatus*(Myxobacteria) Production, Physico-chemical and Biological Properties," The Journal of Antibiotics 48(11)1262-1266 (Nov. 1995).

Hachem et al.; "Serine Protease Activity and Residual LEKTI Expression Determine Phenotype in Netherton Syndrome"; Journal of Investigative Dermatology; 126:1609-1621 (2006).

Hansson et al.; "Epidermal Overexpression of Stratum Corneum Chymotryptic Enzyme in Mice: A Model for Chronic Itchy Dermatitis"; J. Invest. Dermatol.; 118(3):444-449 (2002).

Vasilopoulos et al., "Genetic Association Between an AACC Insertion in the 3'UTR of the Stratum Corneum Chymotryptic Enzyme Gene and Atopic Dermatitis"; J. Invest. Dermatol.; 123:62-66 (2004).

\* cited by examiner

SEQUENCE LISTING

```
<160> NUMBER OF SEQ ID NOS: 1

<210> SEQ ID NO 1
<211> LENGTH: 12
<212> TYPE: PRT
<213> ORGANISM: Homo sapiens
<220> FEATURE:
<221> NAME/KEY: SITE
<222> LOCATION: (2)..(2)
<223> OTHER INFORMATION: Flurophore EDANS attached to residue.
<220> FEATURE:
<221> NAME/KEY: SITE
<222> LOCATION: (11)..(11)
<223> OTHER INFORMATION: Flurophore DABCYL attached to residue.

<400> SEQUENCE: 1

Glu Asp Lys Pro Ile Leu Phe Arg Leu Gly Lys Glu
1               5                   10
```

USE OF CYCLIC DEPSIPEPTIDES TO INHIBIT KALLIKREIN 7

This application is a U.S. National Phase filing of International Serial No. PCT/EP2008/060693 filed Aug. 14, 2008, and claims priority to EP Application Serial No. 07114505.6 filed Aug. 17, 2007, the contents of which are incorporated herein by reference in their entirety.

FIELD OF THE INVENTION

The present invention relates to cyclic depsipeptides, or a derivatives thereof.

BACKGROUND OF THE INVENTION

Kallikrein 7 is a S1 serine protease of the kallikrein gene family displaying a chymotrypsin like activity. Human kallikrein 7 (hK7, KLK7 or stratum corneum chymotryptic enzyme (SCCE), Swissprot P49862) plays an important role in skin physiology (1, 2, 3). It is mainly expressed in the skin and has been reported to play an important role in skin physiology. hK7 is involved in the degradation of the intercellular cohesive structures in cornified squamous epithelia in the process of desquamation. The desquamation process is well regulated and delicately balanced with the de novo production of corneocytes to maintain a constant thickness of the stratum corneum, the outermost layer of the skin critically involved in skin barrier function. In this regard, hK7 is reported to be able to cleave the corneodesmosomal proteins corneodesmosin and desmocollin 1 (4, 5, 6). The degradation of both corneodesmosomes is required for desquamation. In addition, very recently it has been shown that the two lipid processing enzymes β-glucocerebrosidase and acidic sphingomyelinase can be degraded by hK7 (7). Both lipid processing enzymes are co-secreted with their substrates glucosylceramides and sphingomyelin and process these polar lipid precursors into their more non-polar products e.g. ceramides, which are subsequently incorporated into the extracellular lamellar membranes. The lamellar membrane architecture is critical for a functional skin barrier. Finally, hK7 has been shown to activate Interleukin-1β (IL-1β) precursor to its active form in vitro (8). Since keratinocytes express IL-1β but not the active form of the specific IL-1β converting enzyme (ICE or caspase 1), it is proposed that IL-1β activation in human epidermis occurs via another protease, a potential candidate being hK7.

Recent studies link an increased activity of hK7 to inflammatory skin diseases like atopic dermatitis, psoriasis or Netherton's syndrome. This might lead to an uncontrolled degradation of corneodesmosomes resulting in a miss-regulated desquamation, an enhanced degradation of lipid processing enzymes resulting in a disturbed lamellar membrane architecture or an uncontrolled activation of the proinflammatory cytokine IL-1β. The net result would be an impaired skin barrier function and inflammation (see also WO-A-2004/108139).

Due to the fact that the hK7 activity is controlled at several levels, various factors might be responsible for an increased hK7 activity in inflammatory skin diseases. Firstly, the amount of protease being expressed might be influenced by genetic factors. Such a genetic link, a polymorphism in the 3'-UTR in the hK7 gene, was recently described (9). The authors hypothesise that the described 4 base pair insertion in the 3'-UTR of the kallikrein 7 gene stabilizes the hK7 mRNA and results in an overexpression of hK7. Secondly, since hK7 is secreted via lamellar bodies to the stratum corneum extracellular space as zymogen and it is not able to autoactivate, it needs to be activated by another protease e.g. hK5 (5). Uncontrolled activity of such an activating enzyme might result in an overactivation of hK7. Thirdly, activated hK7 can be inhibited by natural inhibitors like LEKTI, ALP or elafin (10, 11). The decreased expression or the lack of such inhibitors might result in an enhanced activity of hK7. Recently it was found, that mutations in the spink5 gene, coding for LEKTI, are causative for Netherton's syndrome (12) and a single point mutation in the gene is linked to atopic dermatitis (13, 14). Finally, another level of controlling the activity of hK7 is the pH. hK7 has a neutral to slightly alkaline pH optimum (2) and there is a pH gradient from neutral to acidic from the innermost to the outermost layers in the skin. Environmental factors like soap might result in a pH increase in the outermost layers of the stratum corneum towards the pH optimum of hK7 thereby increasing the hK7 activity.

The hypothesis that an increased activity of hK7 is linked to skin diseases with an impaired skin barrier including inflammatory and hyperpoliferative skin diseases is supported by the following studies: Firstly, Netherton's syndrome patients show a phenotype dependent increase in serine protease activity, a decrease in corneodesmosomes, a decrease in the lipid processing enzymes β-glucocerebrosidase and acidic sphingomyelinase, and an impaired barrier function (15, 16). Secondly, a transgenic mice overexpressing human kallikrein 7 shows a skin phenotype similar to that found in patients with atopic dermatitis (17, 18, 19). Thirdly, in the skin of atopic dermatitis and psoriasis patients elevated levels of hK7 were described (17, 20). Furthermore, increased activity of K7 and thus epithelial barrier dysfunction may also play an important role in the pathology of other epithelial diseases such as inflammatory bowel disease and Crohn's disease.

Therefore, hK7 is considered to be a potential target for the treatment of diseases involved with epithelial dysfunction such as inflammatory and/or hyperpoliferative and pruritic skin diseases like atopic dermatitis, psoriasis, Netherton's syndrome or other pruritic dermatoses such as prurigo nodularis, unspecified itch of the elderly as well as other diseases with epithelial barrier dysfunction such as inflammatory bowel disease and Crohn's disease and there is a need for specific modulators (agonists or inhibitors) thereof.

Treatment can be by local or systemic application such a creams, ointments and suppositories or by oral or sc or iv application, respectively.

*Chondromyces* is a genus in the family Polyangiaceae, which belongs to the order Myxococcales within the Deltaproteobacteria. Bacteria of the order Myxococcales, also called myxobacteria, are gram-negative rod-shaped bacteria with two characteristics distinguishing them from most other bacteria. They swarm on solid surfaces using an active gliding mechanism and aggregate to form fruiting bodies upon starvation (Kaiser (2003)). The present inventors have identified cyclic depsipeptide produced by *Chondromyces* that are able to specifically modulate kallikrein 7.

SUMMARY OF THE INVENTION

The present invention relates to cyclic depsipeptides, or a derivative thereof, having the structure of formula (I):

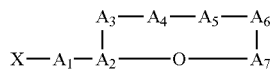

wherein the ester bond is found between the carboxy group of A7 and the hydroxy group of A2, wherein X and $A_1$ are each independently optional, and wherein X is any chemical residue $A_1$ is a standard amino acid, $A_2$ is threonine or serine or 5-methylhydroxyproline, $A_3$ is a non-basic standard amino acid or a non-basic non-standard amino acid, or a non-basic derivative thereof, $A_4$ is Ahp, dehydro-AHP, proline or a derivative thereof, $A_5$ is isoleucine, leucine, phenylalanin, prolin, threonine, or valine, $A_6$ is alanine, phenylalanine, tryptophan, tyrosine or a derivative thereof, $A_7$ is leucine, isoleucine or valine, or a pharmaceutically acceptable salt of cyclic depsipeptide or a derivative thereof, for use as a medicament to treat a kallikrein 7-dependent disease.

Preferably, the kallikrein 7-dependent disease is selected from the group consisting of Netherton's syndrome, pruritic dermatoses such as prurigo nodularis, pustular psioriasis, and cancer, in particular ovarian cancer.

DETAILED DESCRIPTION OF THE INVENTION

Figure 1:
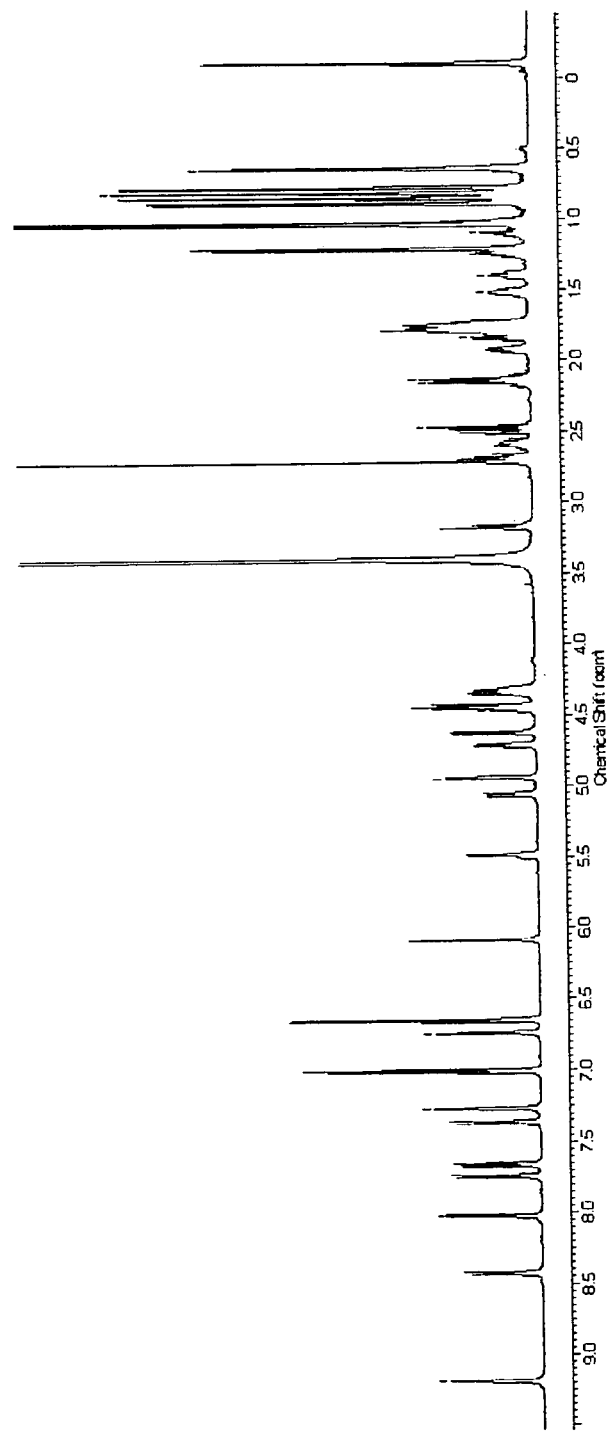
FIG. 1: $^1$H-NMR spectrum of compounds of formula (II) (600 MHz, $d_6$-DMSO)
Figure 2:
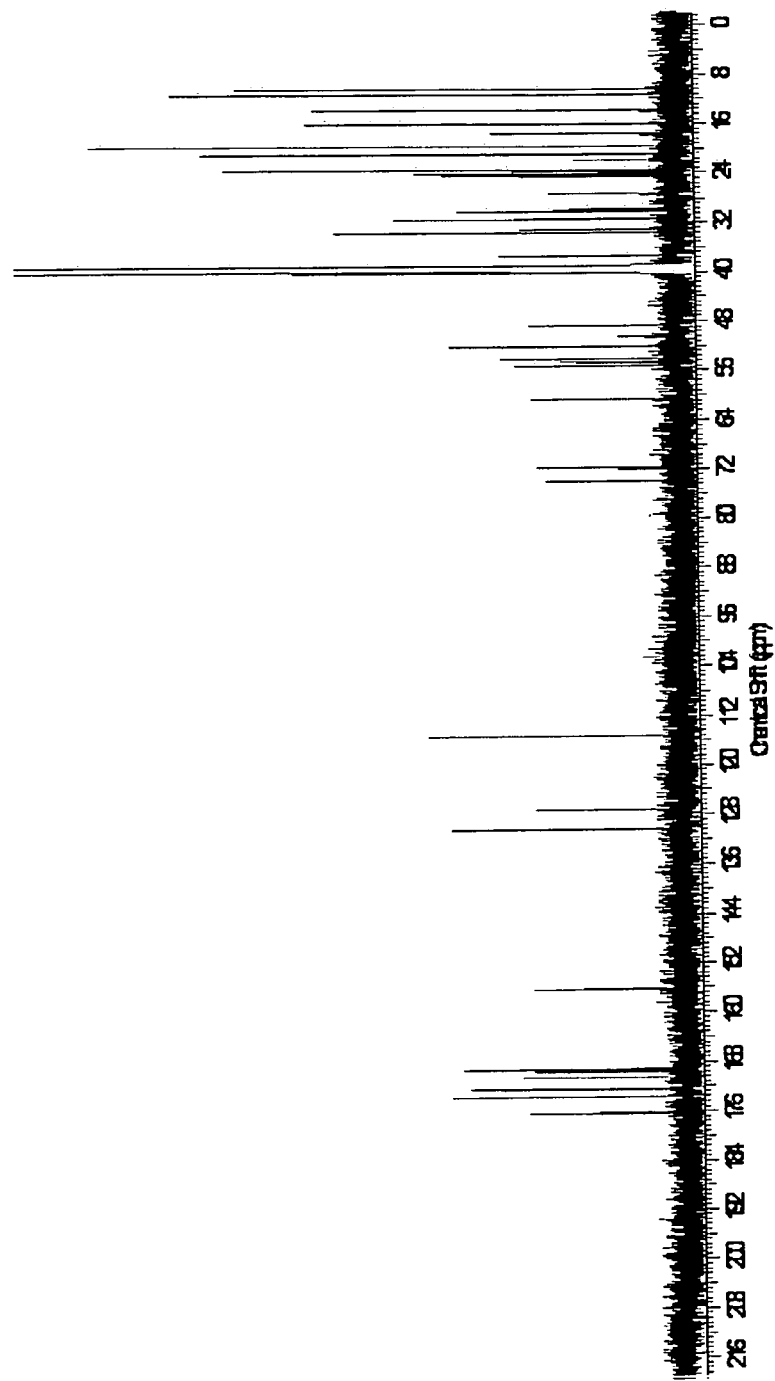
FIG. 2: $^{13}$C-NMR spectrum of compounds of formula (II) (150 MHz, $d_6$-DMSO)
Figure 3:
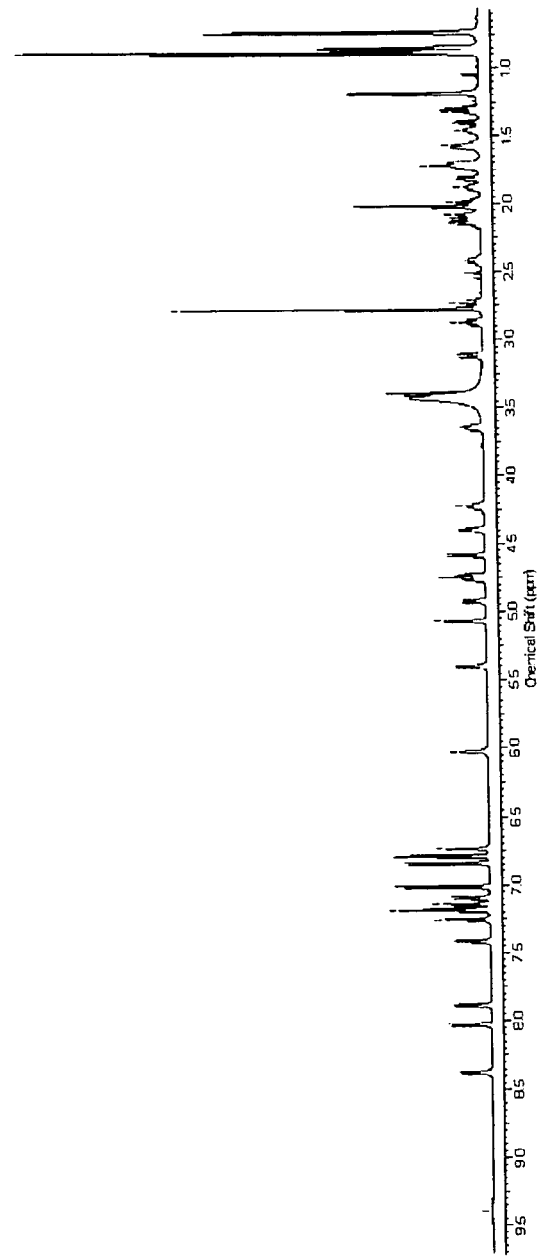
FIG. 3: $^1$H-NMR spectrum of compounds of formula (VIII) (600 MHz, $d_6$-DMSO)
Figure 4:
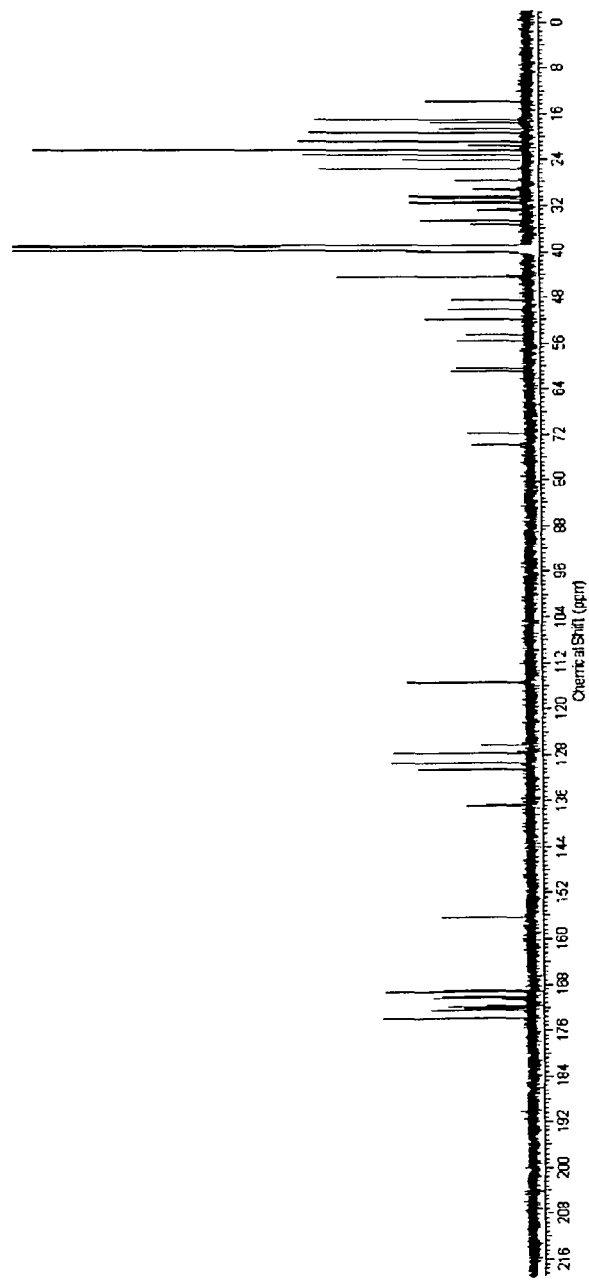
FIG. 4: $^{13}$C-NMR spectrum of compounds of formula (VIII) (150 MHz, $d_6$-DMSO).
Figure 5:
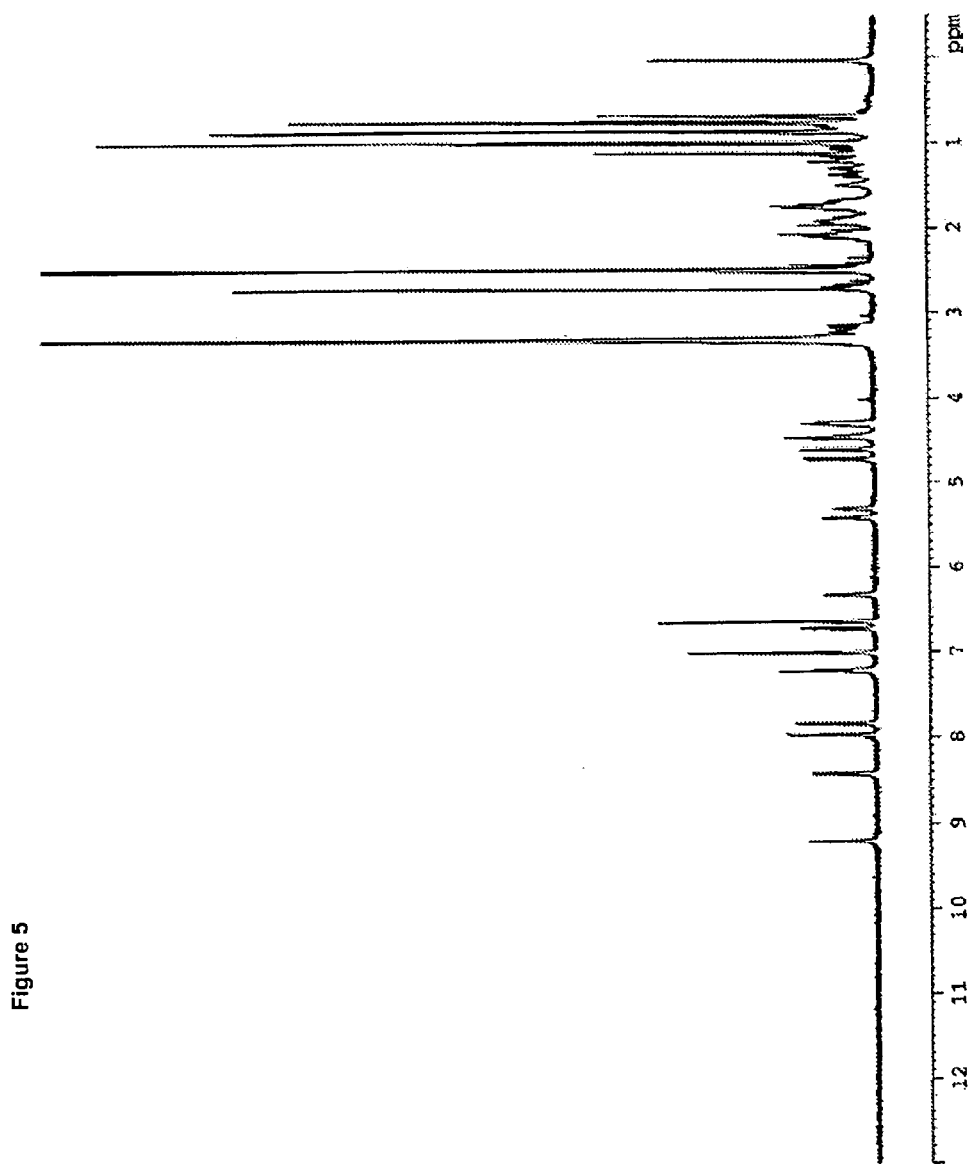
FIG. 5: $^1$H-NMR spectrum of a derivative of the cyclic depsipeptide according to formula (II) wherein the Ahp has been converted into 3-amino-2-piperidone (Example 4).
Figure 6:
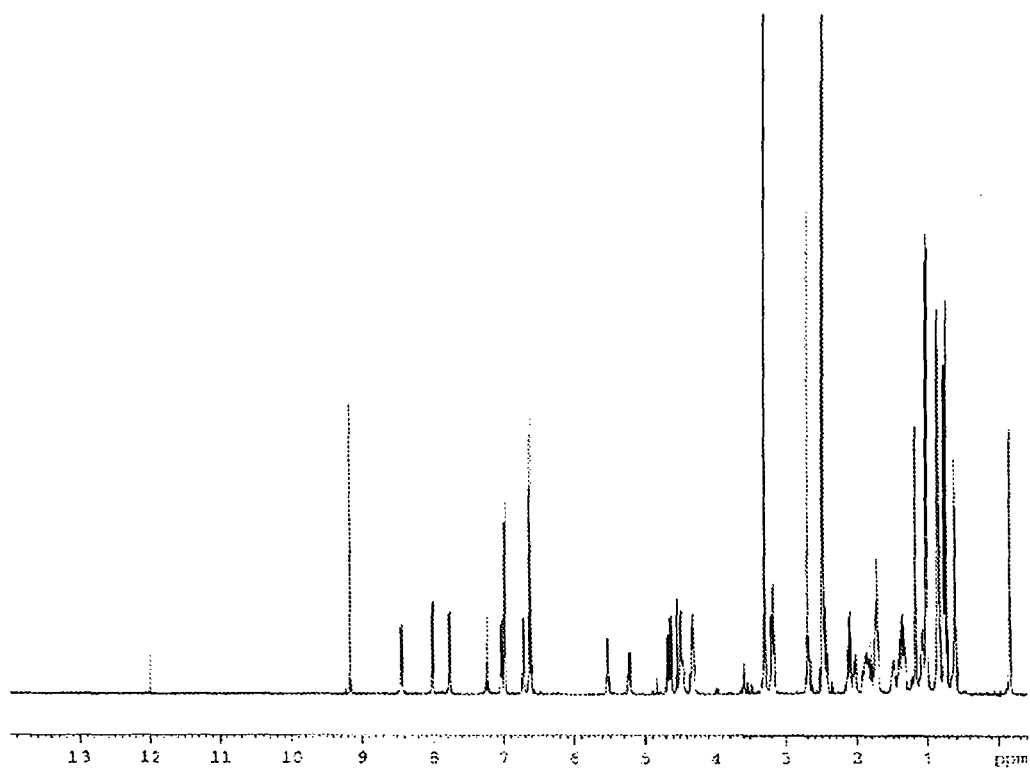
FIG. 6: $^1$H NMR spectrum of a derivative of the cyclic depsipeptide according to Example 5.
Figure 7:
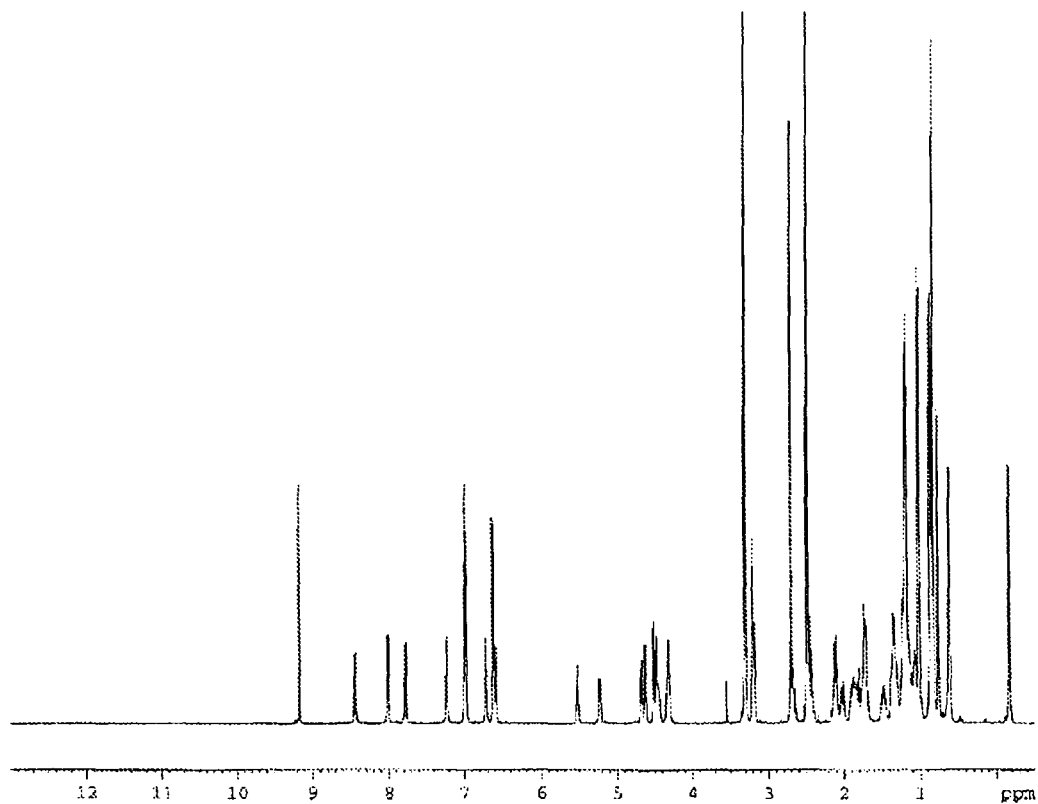
FIG. 7: $^1$H-NMR spectrum of a derivative of the cyclic depsipeptide according to Example 6.
Figure 8:
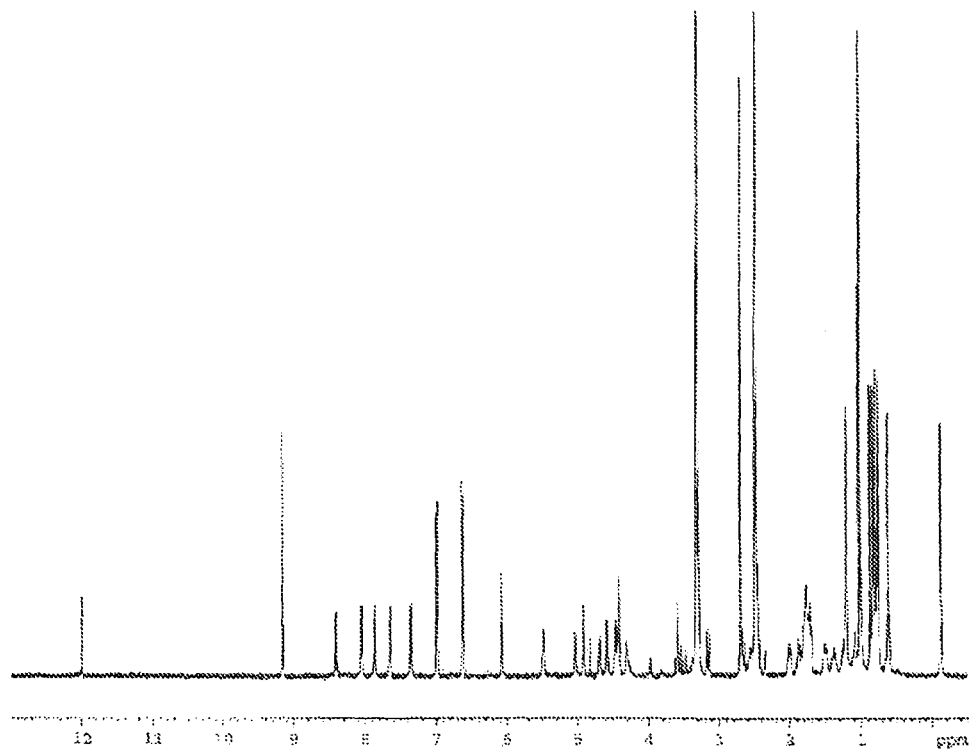
FIG. 8: $^1$H-NMR spectrum of a derivative of the cyclic depsipeptide according to Example 7.

As described herein-above and in the claims, the present invention relates to cyclic depsipeptides, or a derivative thereof, having the structure of formula (I):

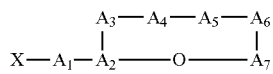

wherein the ester bond is found between the carboxy group of A7 and the hydroxy group of A2, wherein X and $A_1$ are each independently optional, and wherein X is any chemical residue $A_1$ is a standard amino acid, $A_2$ is threonine or serine or 5-methylhydroxyproline, $A_3$ is a non-basic standard amino acid or a non-basic non-standard amino acid, or a non-basic derivative thereof, $A_4$ is Ahp, dehydro-AHP, proline or a derivative thereof, $A_5$ is isoleucine, leucine, phenylalanin, prolin, threonine, or valine, $A_6$ is alanine, phenylalanine, tryptophan, tyrosine or a derivative thereof, $A_7$ is leucine, isoleucine or valine, or a pharmaceutically acceptable salt of cyclic depsipeptide or a derivative thereof, for use as a medicament to treat a kallikrein 7-dependent disease.

Preferably, the kallikrein 7-dependent disease is selected from the group consisting of Netherton's syndrome, pruritic dermatoses such as prurigo nodularis, pustular psioriasis, and cancer, in particular ovarian cancer.

Specific embodiments of cyclic depsipeptides of the invention are:

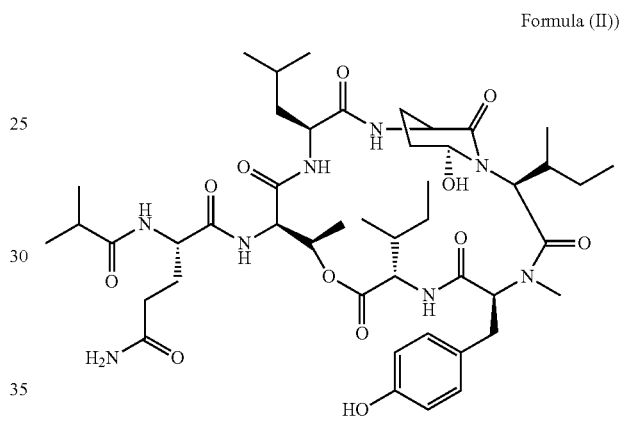

Formula (II)

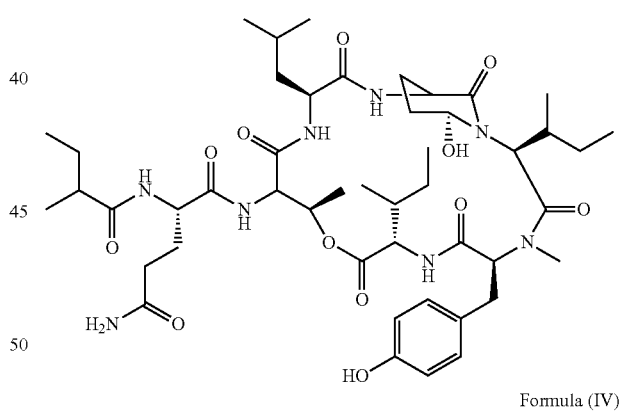

Formula (III)

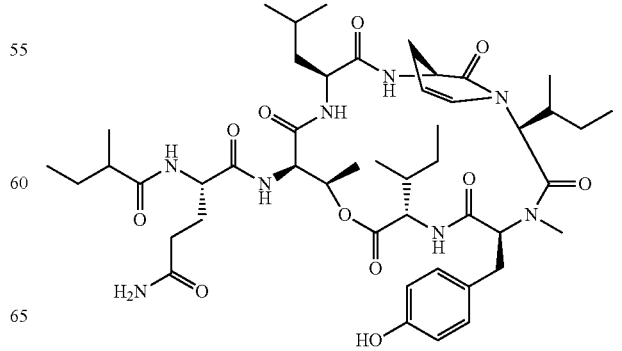

Formula (IV)

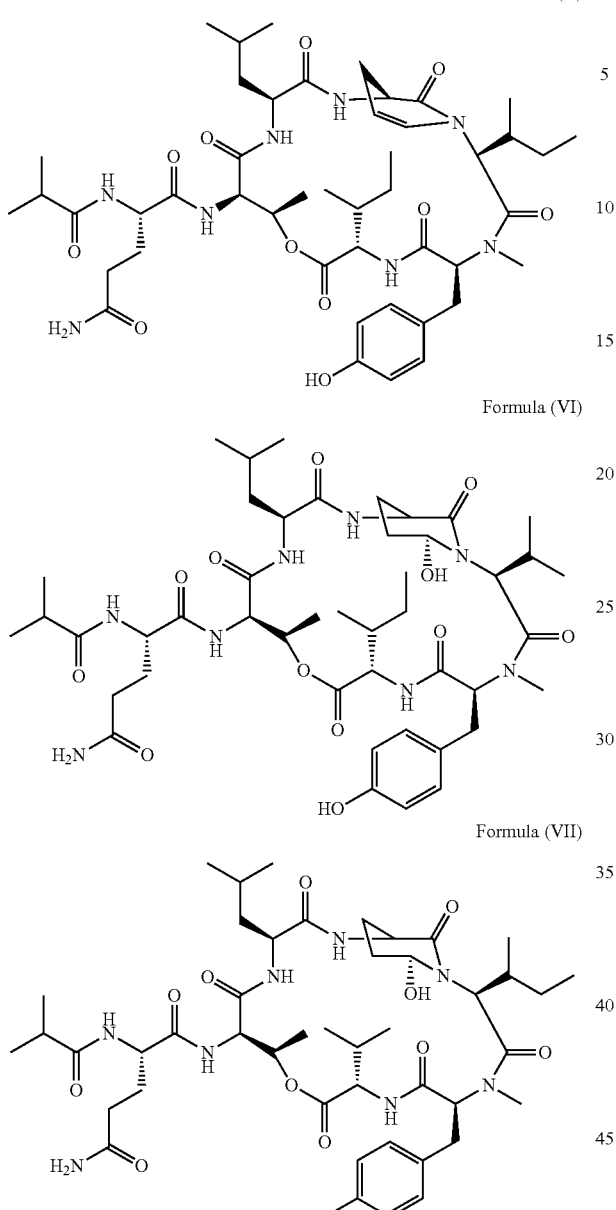

The cyclic depsipetpides of formula (II)-(VII) can be produced by the *Chondromyces crocatus* strain of the invention (DSM 19329).

Other specific embodiments of cyclic depsipeptides of the invention are:

The cyclic depsipetpides of formula (VIII)-(X) can be produced by the *Chondromyces robustus* of the invention (DSM 19330).

Further specific embodiments of the cyclic depsipeptides of the present invention are:

TABLE 1

| Compound name | CAS number |
| --- | --- |
| Lyngbyastatin 4 | 928202-70-4 |
| Micropeptin KT946 | 925421-06-3 |

TABLE 1-continued

| Compound name | CAS number |
| --- | --- |
| Cyanopeptolin 1021 | 914606-83-0 |
| Cyanopeptolin 993 | 914606-81-8 |
| Cyanopeptolin 1063 | 912460-67-4 |
| Largamide G | 911297-59-1 |
| Largamide F | 911297-58-0 |
| Largamide E | 911297-57-9 |
| Largamide D | 911297-56-8 |
| Cyanopeptolin 954 | 866718-63-0 |
| no name | 861388-86-5 |
| no name | 848891-15-6 |
| no name | 848888-25-5 |
| no name | 848780-62-1 |
| no name | 848780-61-0 |
| Micropeptin 88Y | 844636-95-9 |
| Micropeptin 88N | 844636-94-8 |
| Cyanopeptolin 963A | 790300-44-6 |
| no name | 745771-53-3 |
| no name | 685502-64-1 |
| Hofmannolin | 640269-42-7 |
| Planktopeptin BL 1061 | 637300-26-6 |
| Planktopeptin BL 843 | 637300-24-4 |
| Planktopeptin BL 1125 | 637300-22-2 |
| Tasipeptin B | 546123-47-1 |
| Tasipeptin A | 546123-46-0 |
| Nostopeptin BN920 | 501903-96-4 |
| no name | 500145-57-3 |
| Scyptolin B | 403479-63-0 |
| Scyptolin A | 403479-62-9 |
| no name | 370867-67-7 |
| no name | 370867-66-6 |
| no name | 370867-65-5 |
| Somamide B | 350811-52-8 |
| Somamide B | 350811-51-7 |
| Micropeptin SD 1002 | 344939-97-5 |
| Micropeptin SD 979 | 344939-95-3 |
| Oscillapeptilide 97B | 264909-20-8 |
| Oscillapeptilide 97A | 264909-19-5 |
| Micropeptin T 1 | 249730-25-4 |
| Micropeptin SF 909 | 248582-49-2 |
| Oscillapeptin E | 239088-24-5 |
| Oscillapeptin D | 239088-21-2 |
| Oscillapeptin C | 239088-18-7 |
| Oscillapeptin B | 239088-16-5 |
| Nostopeptin D | 227930-54-3 |
| Nostopeptin C | 227930-53-2 |
| Nostopeptin J | 227930-51-0 |
| Nostopeptin I | 227930-50-9 |
| Nostopeptin F | 227930-47-4 |
| Nostopeptin E | 227930-46-3 |
| Symplostatin 2 | 225915-64-0 |
| Micropeptin 88D derivat | 208040-93-1 |
| Micropeptin 88D triacetat | 208040-91-9 |
| Micropeptin 88F | 208040-86-2 |
| Micropeptin 88E | 208040-84-0 |
| Micropeptin 88D | 208040-82-8 |
| Micropeptin 88C | 208040-80-6 |
| Micropeptin 88B | 208040-78-2 |
| Micropeptin 88A | 208040-76-0 |
| Micropeptin 103 | 190771-26-7 |
| Nostopeptin B | 185980-89-6 |
| Nostocyclin | 181622-50-4 |
| FR134043 | 177079-46-8 |
| Anabaenopeptilide 202B | 173450-69-6 |
| Anabaenopeptilide 90B | 173450-68-5 |
| Anabaenopeptilide 202a | 173429-63-5 |
| Anabaenopeptilide 90A | 173429-62-4 |
| Oscillapeptin G | 172548-91-3 |
| Oscillapeptin A | 167172-72-7 |
| Nostopeptin A | 157744-21-3 |
| Microcystilide A | 157242-32-5 |
| Aeruginopeptin 917S-B | 157231-94-2 |
| Aeruginopeptin 917S-C | 157203-82-2 |
| Cyanopeptolin D | 630410-94-5 |
| Cyanopeptolin C | 152839-30-0 |
| Aeruginopeptin 228B | 152510-34-4 |
| Aeruginopeptin 228A | 152510-33-3 |
| Aeruginopeptin 95B | 152510-32-2 |
| Aeruginopeptin 95A | 152510-31-1 |

TABLE 1-continued

| Compound name | CAS number |
| --- | --- |
| FR 901277 | 134170-88-0 |
| Dolastatin 13 | 120231-23-4 |
| Dolastain 13 derivative | 120231-24-5 |
| Dolastain 13 derivative | 125310-66-9 |
| Aspergillicin E | 630410-95-6 |
| Aspergillicin D | 630410-94-5 |
| Aspergillicin C | 630410-92-3 |
| Aspergillicin B | 630410-90-1 |
| Aspergillicin A | 630410-89-8 |
| Nostopeptin K | 227930-52-1 |
| Nostopeptin H | 227930-49-6 |
| Nostopeptin G | 227930-48-5 |
| Ichthyopeptin A | 946828-32-6 |
| Ichthyopeptin B | 946828-33-7 |
| Lyngbyastatin 5 | 957130-98-2 |
| Lyngbyastatin 6 | 957130-99-3 |
| Lyngbyastatin 7 | 957131-00-9 |
| Cyanopeptolin 1138 | 1009081-69-9 |
| no name | 957187-61-0 |
| Cyanopeptolin 984 | 946516-89-8 |
| Micropeptin T20 | 224947-46-0 |

LIST OF ABBREVIATIONS

Ahp 3-amino-6-hydroxy-2-piperidone
DSMZ Deutsche Sammlung von Mikroorganismen and Zellkulturen GmbH
hK7 Human kallikrein 7
HPLC High performance/pressure liquid chromatography
HTS High Throughput Screening
IC Intermediary culture
ID Identification
MB Myxobacteria
MC Main-culture
PC Pre-culture
$pO_2$ Partial pressure of oxygen in culture broth (100%=saturation with air)
rpm Rotations per minute
SCCE Stratum corneum chymotryptic enzyme
SPEX Solid phase extraction
vvm Aeration rate (Volume of air per culture volume and per minute)

A "chemical residue" can be any organic or anorganic chemical moiety. The expression "chemical residue" includes, but is not limited to substituted or unsubstituted aliphatic group, e.g. $C_1$-$C_3$ alkyl, $C_1$-$C_6$ alkyl, or $C_1$-$C_{12}$ alkyl, substituted or unsubstituted aryl, substituted or unsubstituted arylalkyl, substituted or unsubstituted heteroaryl, or halogen. For instance, a chemical residue as defined in the claims can be any of the chemical groups described herein-below.

The expression "chemical residue" includes, but is not limited to amino acids, peptides, polypeptides, proteins and the like.

Examples of anorganic chemical moiety are for instance halogens, such as Br or Cl.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The terms "$C_1$-$C_3$ alkyl," "$C_1$-$C_6$ alkyl," or "$C_1$-$C_{12}$ alkyl," as used herein, refer to saturated, straight- or branched-chain hydrocarbon radicals containing between one and three, one and twelve, or one and six carbon atoms, respectively. Examples of $C_1$-$C_3$ alkyl radicals include methyl, ethyl, propyl and isopropyl radicals; examples of $C_1$-$C_6$ alkyl radicals include, but are not limited to, methyl, ethyl, propyl, isopropyl, n-butyl, tert-butyl, sec-butyl, n-pentyl, neopentyl and n-hexyl radicals; and examples of $C_1$-$C_{12}$ alkyl radicals include, but are not limited to, ethyl, propyl, isopropyl, hexyl, heptyl, octyl, nonyl, decyl, undecyl, dodecyl radicals and the like.

The term "substituted alkyl," as used herein, refers to an alkyl, such as a $C_1$-$C_{12}$ alkyl or $C_1$-$C_6$ alkyl group, substituted by one, two, three or more aliphatic substituents. Suitable aliphatic substituents include, but are not limited to, —F, —Cl, —Br, —I, —OH, protected hydroxy, aliphatic ethers, aromatic ethers, oxo, —$NO_2$, —CN, —$C_1$-$C_{12}$-alkyl optionally substituted with halogen (such as perhaloalkyls), $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-hetero O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$CO_2$—$C_1$-$C_{12}$-alkyl, —$CO_2$—$C_2$-$C_{12}$-alkenyl, —$CO_2$—$C_2$-$C_{12}$-alkynyl, —$CO_2$—$C_3$-$C_{12}$-cycloalkyl, —$CO_2$-aryl, —$CO_2$-heteroaryl, —$CO_2$-hetero cycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NR_2$, NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NR-heteroaryl, —NHC(S)NH-heterocycloalkyl, —NHC(NH)$NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)-1-$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NR)NH—$C_1$-$C_{12}$-alkyl, —C(NH)NH—$C_2$-$C_{12}$-alkenyl, —C(NR)NH—$C_2$-

$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl I, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "$C_2$-$C_{12}$ alkenyl" or "$C_2$-$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "$C_2$-$C_{12}$ alkenyl" or "$C_2$-$C_6$ alkenyl" group as previously defined, substituted by one, two, three or more aliphatic substituents.

The terms "$C_2$-$C_{12}$ alkynyl" or "$C_2$-$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$-$C_{12}$ alkynyl" or "$C_2$-$C_6$ alkynyl" group as previously defined, substituted by one, two, three or more aliphatic substituents. The term "$C_1$-$C_6$ alkoxy," as used herein, refers to a $C_1$-$C_6$ alkyl group, as previously defined, attached to the parent molecular moiety through an oxygen atom. Examples of $C_1$-$C_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by one, two, three or more aromatic substituents.

Aromatic substituents include, but are not limited to, —F, —Cl, —Br, —I, —OH, protected hydroxy, aliphatic ethers, aromatic ethers, oxo, —$NO_2$, —CN, —$C_1$-$C_{12}$-alkyl optionally substituted with halogen (such as perhaloalkyls), $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkynyl, —O—$C_3$-$C_{12}$-cycloalkyl, —O-aryl, —O-hetero aryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$CO_2$—$C_1$-$C_{12}$-alkyl, —$CO_2$—$C_2$-$C_{12}$-alkenyl, —$CO_2$—$C_2$-$C_{12}$-alkynyl, —$CO_2$—$C_3$-$C_{12}$-cycloalkyl, —$CO_2$-aryl, —$CO_2$-heteroaryl, —$CO_2$-hetero cycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl I, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls and the like can be further substituted.

The term "arylalkyl," as used herein, refers to an aryl group attached to the parent compound via a $C_1$-$C_3$ alkyl or $C_1$-$C_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The term "heteroaryl," as used herein, refers to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The term "substituted heteroaryl," as used herein, refers to a heteroaryl group as previously defined, substituted by one, two, three or four aromatic substituents. The term "$C_3$-$C_{12}$-cycloalkyl," as used herein, denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl.

The term "substituted $C_3$-$C_{12}$-cycloalkyl," as used herein, refers to a $C_3$-$C_{12}$-cycloalkyl group as previously defined, substituted by one, two, three or more aliphatic substituents.

The term "heterocycloalkyl," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocycloalkyl," as used herein, refers to a heterocycloalkyl group, as previously defined, substituted by one, two, three or more aliphatic substituents.

The term "heteroarylalkyl," as used herein, to an heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "$C_1$-$C_3$-alkylamino," as used herein, refers to one or two $C_1$-$C_3$-alkyl groups, as previously defined, attached to the parent molecular moiety through a nitrogen atom. Examples of $C_1$-$C_3$-alkylamino include, but are not limited to, methylamino, dimethylamino, ethylamino, diethylamino, and propylamino.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl)($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COON.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$ alkyl), —C(O)NH$_2$, NHC(O)($C_1$-$C_{12}$ alkyl), N($C_1$-$C_{12}$ alkyl)C(O)($C_1$-$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bn or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic sulfonyls, aliphatic sulfamyls, aromatic sulfamyls, aromatic phosphates and aliphatic phosphates.

An "amino acid" is a molecule that contains both amine and carboxyl functional groups with the general formula NH2CHRCOOH. The term amino acid includes standard amino acids and nonstandard amino acids.

"Standard amino acids" are alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

A "standard amino acid which is not aspartic acid" is selected from the group consisting of alanine, arginine, asparagine, cysteine, glutamic acid, glutamine, glycine, histidine, isoleucine, leucine, lysine, methionine, phenylalanine, proline, serine, threonine, tryptophan, tyrosine, and valine.

"Nonstandard amino acids" are amino acids (molecules that contains both amine and carboxyl functional groups) which are not one of the standard amino acids. Examples thereof are selenocysteine (incorporated into some proteins at a UGA codon), pyrrolysine (used by some methanogenic bacteria in enzymes to produce methane and coded for with the codon UAG), lanthionine, 2-aminoisobutyric acid, dehydroalanine, 3-amino-6-hydroxy-2-piperidone, gamma-aminobutyric acid, ornithine, citrulline, homocysteine, dopamine or hydroxyproline.

"Non-basic standard amino acids" are alanine, asparagine, aspartic acid, cysteine, glutamic acid, glutamine, glycine, isoleucine, leucine, methionine, phenylalanine, proline, serine, threonine, tryptophan, tyrosine, and valine.

"Ahp" (3-amino-6-hydroxy-2-piperidone) is a nonstandard amino acid found for instance in cyanobacteria. "Ahp derivatives" include, but are not limited to 3-amino-5,6-dihydro-2-piperidone (dehydro-AHP), 3-amino-2-piperidone and "ether and ester derivatives of AHP. A preferred Ahp derivative is 3-amino-2-piperidone.

Different members of this family of nonstandard amino acids are:

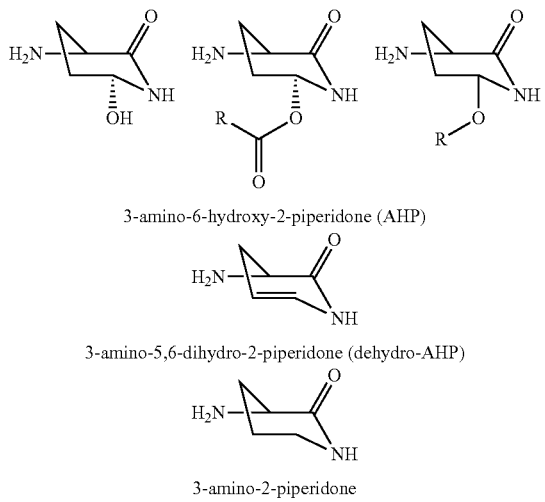

3-amino-6-hydroxy-2-piperidone (AHP)

3-amino-5,6-dihydro-2-piperidone (dehydro-AHP)

3-amino-2-piperidone

"Amino acid derivatives" include, but are not limited to, O-alkyl, O-aryl, O-acyl, S-alkyl, S-aryl, S—S-alkyl, alkoxycarbonyl, O-carbonyl-alkoxy, carbonate, O-carbonyl-aryloxy, O-carbonyl-alkylamino, O-carbonyl-arylamino, N-alkyl, N-dialkyl, N-trialkylammonium, N-acyl, N-carbonyl-alkoxy, N-carbonyl-aryloxy, N-carbonyl-alkylamino, N-carbonyl-arylamino, N-sulfonylalkyl, or N-sulfonylaryl.

"Non-basic standard amino acid derivatives" include, but are not limited to, O-alkyl, O-aryl, O-acyl, S-alkyl, S-aryl, S—S-alkyl, alkoxycarbonyl, O-carbonyl-alkoxy, carbonate, O-carbonyl-aryloxy, O-carbonyl-alkylamino, O-carbonyl-arylamino, N-alkyl, N-dialkyl, N-trialkylammonium, N-acyl, N-carbonyl-alkoxy, N-carbonyl-aryloxy, N-carbonyl-alkylamino, N-carbonyl-arylamino, N-sulfonylalkyl, or N-sulfonylaryl.

"Tyrosine derivative" include, but are not limited to, —O-alkyl, O-aryl, O-heteroaryl, O-acyl, O—PO$_3$H and O—SO$_3$H, as well as halogenation, in ortho or meta position.

"Depsipeptide derivative" include but are not limited to, depsipeptides modified as described herein and to those specifically described in the examples below. Said derivatives can be prepared using methods well known in the art.

The invention further relates to pharmaceutically acceptable salts and derivatives of the compounds of the present invention and to methods for obtaining such compounds. One method of obtaining the compound is by cultivating a *Chondromyces*, or a mutant or a variant thereof, under suitable conditions, preferably using the fermentation protocol described herein-below.

"Salts" of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

The cyclic depsipeptides of the invention inhibit kallikrein 7. An "inhibitor" is a cyclic depsipeptide that inhibits an enzymatic reaction with a measure $IC_{50}$ of less than 100 M, for instance 50 µM, 30 µM, 20 µM or 10 µM. Particularly preferred are cyclic depsipeptides with an $IC_{50}$ of less than 30 µM for human kallikrein 7, for instance cyclic depsipeptides with an $IC_{50}$ of less than 10 µM, 1 µM, 100 nM, 50 nM, 40 nM, 30 nM, 20 nM, 10 nM, or less. $IC_{50}$ for human kallikrein can be measured using the fluorescence-quenched substrate Ac-Glu-Asp(EDANS)-Lys-Pro-Ile-Leu-Phe^Arg-Leu-Gly-Lys (DABCYL)-Glu-$NH_2$ (SEQ ID NO 1) (where ^ indicates the scissile bond, identified by MS analysis) which can be purchased from Biosyntan (Berlin, Germany). Enzymatic reactions are conducted in 50 mM sodium citrate buffer at pH 5.6 containing 150 mM NaCl and 0.05% (w/v) CHAPS. For the determination of $IC_{50}$ values the assay is performed at room temperature in 384-well plates. All final assay volumes are 30 µl. Test compounds are dissolved in 90% (v/v) DMSO/water and diluted in water (containing 0.05% (w/v) CHAPS) to 3-times the desired assay concentration. The 11 final compound concentrations are: 0.3 nM, 1 nM, 3 nM, 10 nM, 30 nM, 100 nM, 300 nM, 1 µM, 3 µM, 10 µM and 30 µM. For each assay, 10 µl water/CHAPS (±test compound) are added per well, followed by 10 µl protease solution (diluted with 1.5× assay buffer). The protease concentration in final assay solution is 0.2 nM (according to the enzyme concentrations determined by the Bradford method). After 1 hour of incubation at room temperature, the reaction is started by addition of 10 µl substrate solution (substrate dissolved in 1.5× assay buffer, final concentration is 2 µM). The effect of the compound on the enzymatic activity is obtained from the linear progress curves and determined from two readings, the first one taken directly after the addition of substrate (t=0 min) and the second one after 1 hour (t=60 min). The $IC_{50}$ value is calculated from the plot of percentage of inhibition vs. inhibitor concentration using non-linear regression analysis software (XLfit, Vers. 4.0; ID Business Solution Ltd., Guildford, Surrey, UK).

Human kallikrein 7 (hK7) is an enzyme with serine protease activity located in the human skin. It was first described as stratum corneum chymotryptic enzyme (SCCE) and may play a role in desquamation of stratum corneum by cleaving proteins of the stratum corneum (e.g., corneodesmosin and plakoglobin). The stratum corneum is the barrier-forming outermost layer of the epidermis and consists of cornified epithelial cells surrounded by highly organized lipids. It is continuously being formed by epidermal differentiation and in normal epidermis the constant thickness of the stratum corneum is maintained by a balance between the proliferation of the keratinocytes and desquamation. Enhanced expression of SCCE in inflammatory skin disease may be of etiological significance (Hansson, et al. (2002)). Transgenic mice expressing human kallikrein 7 in epidermal keratinocytes were found to develop pathologic skin changes with increased epidermal thickness, hyperkeratosis, dermal inflammation, and severe pruritis. A genetic association between a 4 bp (AACC) insertion in the 3'UTR of the stratum corneum chymotryptic enzyme gene and atopic dermatitis has been reported (Vasilopoulos, et al. (2004)), suggesting that the enzyme could have an important role in the development of atopic dermatitis. Atopic dermatitis is a disease with an impaired skin barrier that affects 15%-20% of children. Kallikrein 7 is a S1 serine protease of the kallikrein gene family displaying a chymotrypsin like activity. Human kallikrein 7 (hK7, KLK7 or stratum corneum chymotryptic enzyme (SCCE), Swissprot P49862) plays an important role in skin physiology (1, 2, 3). It is mainly expressed in the skin and has been reported to play an important role in skin physiology. hK7 is involved in the degradation of the intercellular cohesive structures in cornified squamous epithelia in the process of desquamation. The desquamation process is well regulated and delicately balanced with the de novo production of corneocytes to maintain a constant thickness of the stratum corneum, the outermost layer of the skin critically involved in skin barrier function. In this regard, hK7 is reported to be able to cleave the corneodesmosomal proteins corneodesmosin and desmocollin 1 (4, 5, 6). The degradation of both corneodesmosomes is required for desquamation. In addition, very recently it has been shown that the two lipid processing enzymes β-glucocerebrosidase and acidic sphingomyelinase can be degraded by hK7 (7). Both lipid processing enzymes are co-secreted with their substrates glucosylceramides and sphingomyelin and process these polar lipid precursors into their more non-polar products e.g. ceramides, which are subsequently incorporated into the extracellular lamellar membranes. The lamellar membrane architecture is critical for a functional skin barrier. Finally, hK7 has been shown to activate Interleukin-1β (IL-1β) precursor to its active form in vitro (8). Since keratinocytes express IL-1β but not the active form of the specific IL-1β converting enzyme (ICE or caspase 1), it is proposed that IL-1β activation in human epidermis occurs via another protease, a potential candidate being hK7.

Recent studies link an increased activity of hK7 to inflammatory skin diseases like atopic dermatitis, psoriasis or Netherton's syndrome. This might lead to an uncontrolled degradation of corneodesmosomes resulting in a miss-regulated desquamation, an enhanced degradation of lipid processing enzymes resulting in a disturbed lamellar membrane architecture or an uncontrolled activation of the proinflammatory cytokine IL-1β. The net result would be an impaired skin barrier function and inflammation (see also WO-A-2004/108139).

Due to the fact that the hK7 activity is controlled at several levels, various factors might be responsible for an increased hK7 activity in inflammatory skin diseases. Firstly, the amount of protease being expressed might be influenced by genetic factors. Such a genetic link, a polymorphism in the 3'-UTR in the hK7 gene, was recently described (9). The authors hypothesise that the described 4 base pair insertion in the 3'-UTR of the kallikrein 7 gene stabilizes the hK7 mRNA and results in an overexpression of hK7. Secondly, since hK7 is secreted via lamellar bodies to the stratum corneum extracellular space as zymogen and it is not able to autoactivate, it needs to be activated by another protease e.g. hK5 (5). Uncontrolled activity of such an activating enzyme might result in an overactivation of hK7. Thirdly, activated hK7 can be inhibited by natural inhibitors like LEKTI, ALP or elafin (10, 11). The decreased expression or the lack of such inhibitors might result in an enhanced activity of hK7. Recently it was found, that mutations in the spink5 gene, coding for LEKTI, are causative for Netherton's syndrome (12) and a single point mutation in the gene is linked to atopic dermatitis (13, 14). Finally, another level of controlling the activity of hK7 is the pH. hK7 has a neutral to slightly alkaline pH optimum (2) and there is a pH gradient from neutral to acidic from the innermost to the outermost layers in the skin. Environmental factors like soap might result in a pH increase in the outermost layers of the stratum corneum towards the pH optimum of hK7 thereby increasing the hK7 activity.

An increased activity of hK7 is linked to skin diseases with an impaired skin barrier including inflammatory and hyperpoliferative skin diseases. Firstly, Netherton's syndrome patients show a phenotype dependent increase in serine protease activity, a decrease in corneodesmosomes, a decrease in the lipid processing enzymes 6-glucocerebrosidase and acidic sphingomyelinase, and an impaired barrier function (15, 16). Secondly, a transgenic mice overexpressing human kallikrein 7 shows a skin phenotype similar to that found in patients with atopic dermatitis (17, 18, 19). Thirdly, in the skin of atopic dermatitis and psoriasis patients elevated levels of hK7 were described (17, 20). Furthermore, increased activity of K7 and thus epithelial barrier dysfunction may also play an important role in the pathology of other epithelial diseases such as inflammatory bowel disease and Crohn's disease.

Treatment can be by local or systemic application such a creams, ointments and suppositories or by oral or sc or iv application, respectively, in a manner well known in the art.

In one aspect the depsipeptides according to the invention are obtained by cultivating a *Chondromyces crocatus* strain which was deposited on 24 Apr. 2007 with the DSMZ (DSM 19329) or are obtained by cultivating a *Chondromyces robustus* strain which was deposited on 24 Apr. 2007 with the DSMZ (DSM 19330).

The deposit of the strains was made under the terms of the Budapest Treaty on the International Recognition of the Deposit of Microorganisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement.

It is to be understood that the present invention is not limited to cultivation of the particular strains *Chondromyces crocatus* and *Chondromyces robustus*. Rather, the present invention contemplates the cultivation of other organisms capable of producing depsipeptides, such as mutants or variants of the strains that can be derived from this organism by known means such as X-ray irradiation, ultraviolet irradiation, treatment with chemical mutagens, phage exposure, antibiotic selection and the like.

The depsipeptides of the present invention may be biosynthesized by various microorganisms. Microorganisms that may synthesize the compounds of the present invention include but are not limited to bacteria of the order Myxococcales, also referred to as myxobacteria. Non-limiting examples of members belonging to the genera of myxobacteria include *Chondromyces, Sorangium, Polyangium, Byssophaga, Haploangium, Jahnia, Nannocystis, Koffleria, Myxococcus, Corallococcus, Cystobacter, Archangium, Stigmatella, Hyalangium, Melittangium, Pyxicoccus*. The taxonomy of myxobacteria is complex and reference is made to Garrity G M, Bell J Y, Lilburn T G (2004) Taxonomic outline of the prokaryotes, Bergey's manual of systematic bacteriology, $2^{nd}$ edition, release 5.0 May 2004.

The compounds of structural formulas (I-X) are produced by the aerobic fermentation of a suitable medium under controlled conditions via inoculation with a culture of *Chondromyces crocatus* or *Chondromyces robustus*. The suitable medium is preferably aqueous and contains sources of assimilable carbon, nitrogen, and inorganic salts.

Suitable media include, without limitation, the growth media mentioned below in examples 1 and 2. The fermentation is conducted for about 3 to about 20 days at temperatures ranging from about 10° C. to about 40° C.; however for optimum results it is preferred to conduct the fermentation at about 30° C. The pH of the nutrient medium during the fermentation can be about 6.0 to about 9.0.

The culture media inoculated with the depsipeptides producing microorganisms may be incubated under aerobic conditions using, for example, a rotary shaker or a stirred tank fermentor Aeration may be achieved by the injection of air, oxygen or an appropriate gaseous mixture to the inoculated culture media during incubation. As soon as a sufficient amount of the antibiotic compounds have accumulated, they may be concentrated and isolated from the culture in conventional and usual manner, for example by extraction- and chromatographic methods, precipitation or crystallization, and/or in a manner disclosed herein. As an example for extraction, the culture can be mixed and stirred with a suitable organic solvent such as n-butanol, ethyl acetate, cyclohexane, n-hexane, toluene, n-butyl acetate or 4-methyl-2-pentanone, the antibiotic compounds in the organic layer can be recovered by removal of the solvent under reduced pressure. The resulting residue can optionally be reconstituted with for example water, ethanol, methanol or a mixture thereof, and re-extracted with a suitable organic solvent such as hexane, carbon tetrachloride, methylene chloride, dichloromethane or a mixture thereof. Following removal of the solvent, the compounds may be further purified for example by chromatographic methods. As an example for chromatography, stationary phases such as silica gel or aluminia oxide can be applied, with organic eluting solvents or mixtures thereof, including ethers, ketones, esters, halogenated hydrocarbons or alcohols, or reversed-phase chromatography on modified silica gel having various functional groups and eluting with organic solvents or aqueous mixtures thereof, like acetonitrile, methanol or tetrahydrofuran at different pH. Another example is partition-chromatography, for example in the solid-liquid or in the liquid-liquid mode. Also size exclusion chromatography may be applied, for example using Sephadex LH-20 (Sigma-Aldrich) and eluting with different solvents, preferably with alcohols.

As it is usual in this field, the production as well as the recovery and purification process may be monitored by a variety of analytical methods, including bioassays, TLC, HPLC or a combination thereof, and applying different detection methods, for TLC typically UV light, iodine vapour or spraying colouring reagents, for HPLC typically UV light, mass sensitive or light scattering methods. For example a HPLC technique is represented by using a reversed-phase column with a functionalized silica gel and applying an eluent which is a linear gradient mixture of a polar water miscible solvent and water at a specific pH, and a detection method with UV light at different wavelengths and a mass sensitive detector.

The depsipetides biosynthesized by microorganisms may optionally be subjected to random and/or directed chemical modifications to form compounds that are derivatives or structural analogs. Such derivatives or structural analogs having similar functional activities are within the scope of the present invention. Depsipeptides may optionally be modified using methods well-known in the art and described herein.

For instance, derivatives of the depsipeptides of the invention may be prepared by derivatization of cyclic depsipeptides of formula

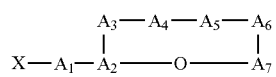

which comprises
a)—the preparation of compounds wherein A4 is

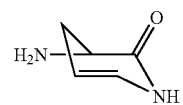

by treatment of a compound wherein A4 is

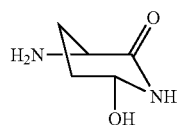

with an organic or inorganic acid, e.g. trifluoro acetic acid, sulphuric acid, hydrochloric acid, or a Lewis acid, e.g. borontrifluoride etherate in a solvent, e.g. dichloromethane, THF, or without a solvent at a temperature between −78° C. and 150° C., preferentially between −30° C. and room temperature.

b)—the preparation of compounds wherein A4 is

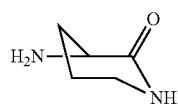

by treatment of a compound wherein A4 is

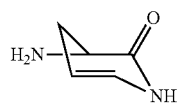

with molecular hydrogen or source thereof, e.g. cyclohexene, ammonium formate, in presence of a catalyst e.g. palladium in a solvent e.g. 2-propanol at a temperature between −50 and 100° C., preferentially at room temperature.

c)—the preparation of compounds wherein A4 is

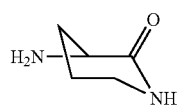

by treatment of a compound wherein A4 is

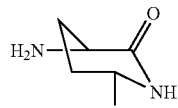

with an organic or inorganic acid, e.g. sulphuric acid, hydrochloric acid or a Lewis acid, e.g. borontrifluoride etherate in presence of an reducing agent, e.g. triethylsilane, a solvent, e.g. dichloromethane, THF, or without a solvent at a temperature between −78° C. and 150° C., preferentially between −50° C. and room temperature.

d)—the preparation of compounds wherein A4 is

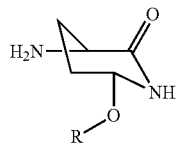

by treatment of a compound wherein A4 is

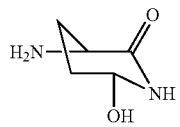

with an substituted or unsubstituted alkanol and an organic or inorganic acid, e.g. trifluoroacetic acid, sulphuric acid, hydrochloric acid, or a Lewis acid, e.g. borontrifluoride etherate in a solvent, e.g. substituted and unsubstituted alkanoles, THF, dichloromethane, preferentially substituted and unsubstituted alkanoles, or without a solvent at a temperature between −78° C. and 150° C., preferentially between −30° C. and room temperature.

Unless otherwise indicated, all numbers expressing quantities of ingredients, properties such as molecular weight, reaction conditions, $IC_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Production of the Compounds of Formula (II)-(VII)

Strain:

The *Chondromyces crocatus* strain was isolated from an environmental sample, rotten wood of a walnut tree, in our laboratories.

The strain has been unambiguously identified as a *Chondromyces crocatus* based on the morphology of the fruiting bodies as well as on the partial sequence of the 16S-RNA gene. *C. crocatus* was assigned to biological risk group 1 by the DSMZ (DSMZ (2007)). *Chondromyces* is a genus in the family Polyangiaceae, which belongs to the order Myxococcales within the Delta-proteobacteria. Bacteria of the order Myxococcales, also called myxobacteria, are gram-negative rod-shaped bacteria with two characteristics distinguishing them from most other bacteria. They swarm on solid surfaces using an active gliding mechanism and aggregate to form fruiting bodies upon starvation (Kaiser (2003)).

The *Chondromyces crocatus* strain of the invention has been deposited at the DSMZ under the accession number 19329.

The *Chondromyces crocatus* strain of the invention is not viable as a pure culture and cannot be maintained without a companion strain. The companion strain can be obtained and maintained as a pure culture by streaking an aliquot of a fermentation co-culture on agar plates (LB medium). A similar observation was made by the Reichenbach group (Jacobi, et al. (1996), Jacobi, et al. (1997)). Based on a partial DNA sequence of the 16S-rRNA gene of the companion strain of *Chondromyces crocatus* of this invention, the closest match is *Bosea thiooxidans* from the order Rhizobiales within the Alpha-proteobacteria. The 424 bp sequence fragment 16S-rRNA investigated has about 98% identity (at least 8 nucleotide exchanges) to sequence AF508112 (*B. thiooxidans*) from genebank. *B. thiooxidans* was isolated from soil samples collected from different agricultural fields around Calcutta, India. It is capable to oxidate reduced inorganic sulfur compounds in the presence of some organic substrates and was described as a novel species and a novel genus in 1996 (Das, et al. (1996)). A phylogenetic tree derived from the partial 16S-RNA sequences of all 5 described *Bosea* species indicates a separate position for the *Bosea* companion strain isolated from *C. crocatus*.

Cultivation:

100 L fermentor cultures were performed according to the following protocol:

Precultures were started by inoculation of 5 ml (=10%) from a liquid culture of *Chondromyces crocatus* strain of the invention into 50 ml of medium MD1 (adapted after Bode et al. 2003, see table 6) in a 200-ml baffled shake flask. After 11 days incubation at 30° C. and 120 rpm on a rotary shaker a 1st intermediate culture was started by inoculation of 10 ml each (=10%) from the preculture into 5×100 ml of medium MD1 in 500-ml baffled shake flasks. After 7 days incubation at 30° C. and 120 rpm on a rotary shaker a 2nd intermediate culture was started by inoculation of 25 ml each (=5%) from the 1st intermediate culture into 19×500 ml of medium MD1 in 2-L nonbaffled shake flasks. After 6 days of incubation at 30° C. and 150 rpm on a rotary shaker the whole 2nd intermediate culture (9.5 liters=9.5%) was used to inoculate 100 liters of production medium POL1 (adapted after Kunze et al. 1995, see table 7)

This 100-L main culture was performed in a 100-L scale steel tank fermentor. Temperature was controlled at 30° C., aeration was 20 l/min (=0.2 vvm) and agitation speed was 50 rpm. A slight overpressure of 0.5 bar was maintained inside of the fermentor vessel. Culture pH was maintained at 6.9-7.1 by controlled addition of $3NH_2SO_4$ or 3N NaOH. After a lag-phase of about 1 day oxygen consumption accelerated for about 4 days indicating exponential growth of the culture. During the last 2 days oxygen consumption was slightly reduced indicating a stationary phase of the culture. After 7 days the culture was harvested with a titer of 5.3 mg/l of a cyclic depsipeptide according to Formula II.

Extraction:

The whole fermentation broth was transferred into a 1600 l steel vessel and decanted for 1 hour. The wet cell pellet (200 g) was harvested from the bottom fraction by filtration through a paper filter. The cell pellet was extracted 3 times by turaxing it 30 minutes each with 10 l ethyl acetate. Then the residual water was separated from the solvent phase. The solvent phase was washed with 5 l water and then evaporated to obtain a dry extract referred to as 'cell extract'.

The culture filtrate was extracted with 200 l ethyl acetate. After 2 hours contact time, including 1 hour of turaxing, the organic phase was separated, washed with 20 l water and finally evaporated to obtain a dry extract referred to as 'culture filtrate extract'.

Compound Isolation:

The culture filtrate extract (4.4 g) was dissolved in 80 mL Methanol. The insoluble ingredients were removed by centrifugation and the supernatant was evaporated to dryness yielding in 3.3 g extract. The extract was dissolved in 7.5 mL MeOH, 3 mL DMSO and 0.5 mL dichloromethane and purified by reversed phase chromatography (Waters Sunfire RP18 10 μm, 30×150 mm) using 0.01% formic acid (solvent A), and acetonitrile containing 0.1% formic acid (solvent B) as solvents The flow rate was 50 mL/min. The gradient is shown in Table 1. The material was purified in 7 chromatographic runs. From each run the collected fractions were analyzed by HPLC, fractions containing the cyclic depsipeptide according to the invention were combined and evaporated in vacuum to dryness. The chromatography yielded in 134 mg cyclic depsipeptide according to formula (II) with a purity of >97% and 80 mg with a purity of 90%.

TABLE 2

HPLC gradient used for purification of the cyclic depsipeptide according to formula (II)

| time (min) | solvent A (%) | solvent B (%) |
|---|---|---|
| 0.0 | 90 | 10 |
| 1.0 | 90 | 10 |
| 23.0 | 50 | 50 |
| 23.1 | 0 | 100 |
| 27.0 | 0 | 100 |
| 27.1 | 90 | 10 |
| 30.0 | 90 | 10 |

TABLE 3

Gradient used for normal phase separation

| time (min) | cyclohexane (%) | ethyl acetate (%) | methanol (%) |
|---|---|---|---|
| 0 | 75 | 25 | 0 |
| 10 | 75 | 25 | 0 |
| 33 | 25 | 75 | 0 |
| 56 | 20 | 70 | 10 |
| 79 | 0 | 50 | 50 |
| 93 | 0 | 50 | 50 |

The cell extract (6.67 g) was dissolved in dichloromethane/methanol 4:1. The solution was filtered and the filtrate was adsorbed on diatom (2 g diatom/1 g extract, ISOLUTE® (Diatomaceous Earth), International Sorbent Technology Ltd., Hengoed Mid Glam, UK) followed by evaporation. The solid residue was loaded on a pre-packed silica gel column (4×18 cm, 90 g silica gel 40-63) and eluted with a gradient of cyclohexane, ethyl acetate and methanol. The gradient is shown in Table 2, the flow rate was 28 ml/min. Fractions volumes of 28 ml were collected. The fractions were combined according to the peaks visible in the UV-trace yielding in 12 pooled fractions (A-L). Fractions containing the depsipeptides (H-J) were further purified using reversed-phase chromatography. The chromatographic method and work up procedure is identical to the purification method described for the culture filtrate. In total 46.1 mg cyclic depsipeptide according to formula (II), 17.9 mg cyclic depsipeptide according to formula (III) and 6.1 mg of a 1:1 mixture of the depsipeptides according to formula (VI) and (VII) have been isolated. The assignment of the structures of compound (VI) and (VII) is based on high resolution MS and the comparison of the $^1$H-NMR data of the mixture of compound (VI) and (VII) with the $^1$H-NMR data of compound (II).

Other cyclic depsipeptide according to formula (II) have also been found at a lesser concentration in the cell extract. Among these other cyclic depsipeptides were those according to formula (IV) and (V).

Characterization of Compounds:
Physical data of compound of formula (II)

IR (KBr pellet): 3337, 3297, 3062, 2966, 2936, 2877, 1736, 1659, 1533, 1519, 1464, 1445, 1410, 1385, 1368, 1249, 1232, 1205, 989, 832 cm$^{-1}$ FT-MS (9.4 T APEX-III): 951.5165. Calc. for $C_{46}H_{72}N_8O_{12}$+Na: 951.5162

$^1$H NMR (600 MHz, d$_6$-DMSO) $\delta_H$: −0.10 (3H, d, J=7.0 Hz), 0.65 (4H, m), 0.78 (3H, d, J=7.0 Hz), 0.82 (3H, t, J=7.2 Hz), 0.85 (3H, d, J=7.0 Hz), 0.89 (3H, d, J=7.0 Hz), 1.02 (1H, m), 1.03 (6H, 2×d, J=7.0 Hz), 1.10 (1H, m), 1.21 (3H, d, J=7.0 Hz), 1.25 (1H, m), 1.40 (1H, m), 1.52 (1H, m), 1.76 (6H, m), 1.84 (1H, m), 1.93 (1H, m), 2.15 (2H, m), 2.48 (1H, m), 2.59 (1H, m), 2.69 (1H, m), 2.72 (3H, s), 3.17 (1H, m), 4.32 (2H, m), 4.44 (2H, m), 4.64 (1H, d, J=9.5 Hz), 4.71 (1H, m), 4.94 (1H, s), 5.06 (1H, m), 5.49 (1H, m), 6.08 (1H, d, J=2.2 Hz), 6.65 (2H, d, J=8.4), 6.74 (1H, s), 7.00 (2H, d, J=8.4 Hz), 7.27 (1H, s), 7.36 (1H, d, J=9.5 Hz), 7.66 (1H, d, J=10.2 Hz), 7.74 (1H, d, J=8.8 Hz), 8.02 (1H, d, J=8.1 Hz), 8.43 (1H, d, J=8.1 Hz), 9.19 (1H, s).

$^{13}$C NMR (150 MHz) d$_6$-DMSO $\delta_C$: 10.35, CH$_3$; 11.22, CH$_3$; 13.79, CH$_3$; 16.00, CH$_3$; 17.63, CH$_3$; 19.49, 2×CH$_3$; 20.83, CH$_3$; 21.72, CH$_2$; 23.30, CH$_3$; 23.70, CH$_2$; 24.16, CH; 24.41, CH$_2$; 27.35, CH$_2$; 29.74, CH$_2$; 30.07, CH$_3$; 31.44, CH$_2$; 33.13, CH; 33.19, CH$_2$; 33.68, CH; 37.39, CH; 39.05, CH$_2$; 48.75, CH; 50.59, CH; 52.01, CH; 54.11, CH; 54.65, CH; 55.24, CH; 60.60, CH; 71.86 CH; 73.89, CH; 115.28, 2×CH; 127.31, Cq; 130.35, 2×CH; 156.25, Cq; 169.09, Cq; 169.25, Cq; 169.34, Cq; 169.74, Cq; 170.60, Cq; 172.41, Cq; 172.52, Cq; 173.78, Cq; 176.32, Cq Physical Data of Compound of Formula (III)

FT-MS (9.4 T APEX-III). Found: 965.5318. Calc. for $C_{47}H_{74}N_8O_{12}$+Na: 965.5318

$^1$H NMR (600 MHz) d$_6$-DMSO $\delta_H$: −0.10 (3H, d, J=7.0 Hz), 0.64 (4H, m), 0.78 (3H, d, J=7.0 Hz), 0.82 (3H, t, J=7.0 Hz), 0.83 (3H, t, J=7.3 Hz), 0.85 (3H, d, J=7.0 Hz), 0.89 (3H, d, J=7.0 Hz), 1.01 (3H, d, J=7.1 Hz), 1.04 (1H, m), 1.10 (1H, m), 1.21 (3H, d, J=7.0 Hz), 1.25 (1H, m), 1.32 (1H, m), 1.40 (1H, m), 1.53 (2H, m), 1.77 (6H, m), 1.84 (1H, m), 1.92 (1H, m), 2.12 (1H, m), 2.16 (1H, m), 2.28 (~1H, m), 2.59 (1H, m), 2.68 (1H, m), 2.72 (3H, s), 3.17 (1H, m), 4.32 (1H, m), 4.38 (1H, m), 4.43 (1H, d, J=10.2 Hz), 4.46 (1H, m), 4.63 (1H, d, J=9.5 Hz), 4.71 (1H, m), 4.94 (1H, m), 5.06 (1H, m), 5.49 (1H, m), 6.11 (1H, s, broad), 6.65 (2H, d, J=8.8 Hz), 6.73 (1H, s), 7.00 (2H, d, J=8.8 Hz), 7.27 (1H, s), 7.37 (1H, d, J=9.5 Hz), 7.66 (1H, d, J=10.2 Hz), 7.75 (1H, d, J=9.7 Hz), 8.07 (1H, d, J=8.1 Hz), 8.45 (1H, d, J=8.8 Hz), 9.24 (1H, broad)

Physical Data of Compound of Formula (IV)

FT-MS (9.4 T APEX-III). Found: 947.5196. Calc. for $C_{47}H_{72}N_8O_{11}$+Na: 947.5213.

$^1$H NMR (600 MHz) d$_6$-DMSO $\delta_H$: 0.08 (3H, d, J=7.0 Hz), 0.68 (3H, t, J=7.2 Hz), 0.71 (3H, d, J=7.0 Hz), 0.78 (3H, d, J=7.0 Hz), 0.83 (3H, t, J=7.3 Hz), 0.84 (1H, m), 0.87 (3H, t, J=7.2 Hz), 0.88 (3H, d, J=7.0 Hz), 0.99 (3H, d, J=7.1 Hz), 1.08 (1H, m), 1.17 (3H, d, J=6.7 Hz), 1.18 (1H, m), 1.31 (2H, m), 1.43 (1H, m), 1.51 (1H, m), 1.54 (1H, m), 1.76 (2H, m), 1.90 (1H, m), 1.94 (1H, m), 2.01 (1H, m), 2.10 (1H, m), 2.16 (1H, m), 2.26 (1H, m), 2.46 (2H, m), 2.73 (1H, m), 2.74 (3H, s), 3.19 (1H, m), 4.34 (1H, m), 4.36 (1H, m), 4.51 (1H, m), 4.55 (1H, m), 4.66 (1H, d, J=10.0 Hz), 4.79 (1H, d, J=11.0 Hz), 5.19 (1H, m), 5.28 (1H, m), 5.44 (1H, m), 6.25 (1H, d, J=7.3 Hz), 6.33 (1H, d, J=8.8 Hz), 6.68 (2H, d, J=8.8 Hz), 6.75 (1H, s), 7.04 (2H, d, J=8.8 Hz), 7.28 (1H, s), 7.32 (1H, d, J=8.8 Hz), 7.91 (1H, d, J=9.5 Hz), 8.05 (1H, d, J=8.1 Hz), 8.57 (1H, d, J=8.9 Hz), 9.38 (1H, broad)

Physical Data of Compound of Formula (V)

FT-MS (9.4 T APEX-III). Found: 933.5053. Calc. for $C_{46}H_{70}N_8O_{11}$+Na: 953.5056

$^1$H NMR (600 MHz) d$_6$-DMSO $\delta_H$: 0.08 (3H, d, J=7.0 Hz), 0.68 (3H, t, J=7.2 Hz), 0.71 (3H, d, J=7.0 Hz), 0.79 (3H, d, J=7.0 Hz), 0.83 (1H, m), 0.88 (3H, t, J=7.2 Hz), 0.89 (3H, d, J=7.0 Hz), 1.01 (3H, d, J=7.0 Hz), 1.03 (3H, d, J=7.0 Hz) 1.08 (1H, m), 1.17 (3H, d, J=6.7 Hz), 1.20 (1H, m), 1.31 (1H, m), 1.42 (1H, m), 1.54 (1H, m), 1.74 (2H, m), 1.91 (2H, m), 2.02 (1H, m), 2.10 (1H, m), 2.15 (1H, m), 2.46 (3H, m), 2.75 (3H, s), 2.76 (1H, m), 3.19 (1H, m), 4.32 (1H, m), 4.34 (1H, m), 4.51 (1H, m), 4.55 (1H, m), 4.66 (1H, d, J=9.5 Hz), 4.79 (1H, d, J=11.0 Hz), 5.19 (1H, m), 5.28 (1H, m), 5.43 (1H, m), 6.25 (1H, d, J=7.0 Hz), 6.33 (1H, d, J=8.5 Hz), 6.68 (2H, d, J=8.8 Hz), 6.75 (1H, s), 7.04 (2H, d, J=8.8 Hz), 7.28 (1H, s), 7.31 (1H, d, J=8.8 Hz), 7.90 (1H, d, J=9.5 Hz), 7.99 (1H, d, J=8.1 Hz), 8.52 (1H, d, J=8.8 Hz), 9.30 (1H, broad)

Example 2

Production of Compound of Formula (VIII, IX, X)

Strain:

The *Chondromyces robustus* strain was isolated from a dung sample. The *Chondromyces robustus* strain of the invention has been identified as a *Chondromyces robustus* based on the morphology of the fruiting bodies as well as on the partial sequence of the 16S-RNA gene. *C. robustus* was assigned to biological risk group 1 by the DSMZ (DSMZ (2007)). *Chondromyces* is a genus in the family Polyangiaceae, which belongs to the order Myxococcales within the Delta-proteobacteria. Bacteria of the order Myxococcales, also called myxobacteria, are gram-negative rod-shaped bacteria with two characteristics distinguishing them from most other bacteria. They swarm on solid surfaces using an active gliding mechanism and aggregate to form fruiting bodies upon starvation (Kaiser (2003)).

The *Chondromyces robustus* strain of the invention has been deposited at the DSMZ under the accession number 19330.

Cultivation:

100 L fermentor cultures were performed according to the following protocol:

Precultures were started by inoculation of 20 ml each (=20%) from a liquid culture of the *Chondromyces robustus* strain of the invention into 6×100 ml of medium MD1 (adapted after Bode et al. 2003) in 500-ml baffled shake flasks. After 1 day of incubation at 30° C. and 120 rpm on a rotary shaker a 1$^{st}$ intermediate culture was started by inoculation of 100 ml each (=25%) from the preculture into 6×400 ml of medium MD1 in 2-L baffled shake flasks. After 3 days incubation at 30° C. and 120 rpm on a rotary shaker a 2$^{nd}$ intermediate culture was started by inoculation of 3 liters (=20%) from the 1st intermediate culture into a 20-L steel tank fermentor containing 15 liters of medium MD1. Temperature was controlled at 30° C., aeration was 20 l/min (=1.0 vvm) and agitation speed was 80 rpm. A slight overpressure of 0.5 bar was maintained inside of the fermentor vessel. Although there was no pH control the pH of the culture decreased only slightly from pH 6.95 at start to pH 6.88 on day 7. After 7 days the whole 2nd intermediate culture (18 liters=20%) was used to inoculate 90 liters of production medium POL1 (adapted after Kunze et al. 1995) (starting volume=108 liters). The main culture was performed in a 100-L scale steel tank fermentor. Temperature was controlled at 30° C., aeration was 30 l/min (=0.3 vvm) and agitation speed was in the beginning 50 rpm and after 4 days 80 rpm. A slight overpressure of 0.5 bar was maintained inside of the fermentor vessel. Culture pH was maintained at 6.8-7.2 by controlled addition of $2NH_2SO_4$ or 1.5N NaOH. After 14 days the culture was harvested with a titer of 3 mg/l.

Extraction:

The whole fermentation broth was transferred into a 1600 l steel vessel and decanted for 1 hour. The wet cell pellet (about 200 g) was harvested from the bottom fraction by filtration through a paper filter. The cell pellet was extracted 3 times by turaxing it 30 minutes each with 10 l ethyl acetate. Then the residual water was separated from the solvent phase. The solvent phase was washed with 5 l water and then evaporated to obtain 11.9 g dry extract referred to as 'cell extract'.

The culture filtrate was extracted with 200 l ethyl acetate. After 2 hours contact time, including 1 hour of turaxing, the organic phase was separated, washed with 20 l water and finally evaporated to obtain 12.5 g of dry extract referred to as 'culture filtrate extract'.

Compound Isolation:

Each extract (from mycelium and culture filtrate) was dissolved in dichloromethane/methanol 4:1. The solution was filtered and the filtrate was adsorbed on diatom (2 g diatom/1 g extract, ISOLUTE® (Diatomaceous Earth), International Sorbent Technology Ltd., Hengoed Mid Glam, UK) followed by evaporation. The solid residue was loaded on a pre-packed silica gel column (4×18 cm, 100 g silica gel 40-63) and eluted with a gradient of cyclohexane, ethyl acetate and methanol. The gradient is shown in Table 4, the flow rate was 28 ml/min. Fractions volumes of 28 ml were collected. The fractions were combined according to the peaks visible in the UV-trace. The fraction containing the cyclic depsipeptide of the invention was further purified using reversed-phase chromatography (Waters Sunfire RP18 10 µm, 30×150 mm) using 0.01% formic acid (solvent A), and acetonitrile containing 0.1% formic acid (solvent B) as solvents. The flow rate was 50 mL/min. The gradient is shown in Table 5. For injection the material was dissolved in MeOH/DMSO 1:1 (concentration 200 mg/mL). The collected fractions were analyzed by HPLC, fractions containing the cyclic depsipeptide of the invention were combined and evaporated in vacuum to dryness. The chromatography of the extract yielded in 52 mg pure (>97%) cyclic depsipeptide according to formula (VIII) A total of 85 mg pure cyclic depsipeptide according to formula (VIII) could be isolated from the combined extracts.

Other cyclic depsipeptide according to formula (VIII) have also been found at a lesser concentration in the cell extract. Among these other cyclic depsipeptides were those according to formula (IX) and (X).

TABLE 4[a]

Gradient used for normal phase separation[b]

| time (min) | cyclohexane (%) | ethyl acetate (%) | methanol (%) |
|---|---|---|---|
| 0 | 75 | 25 | 0 |
| 10 | 75 | 25 | 0 |
| 33 | 25 | 75 | 0 |
| 56 | 20 | 70 | 10 |
| 79 | 0 | 50 | 50 |
| 93 | 0 | 50 | 50 |

TABLE 5[c]

HPLC gradient used for purification of cyclic depsipeptide according to formula (VIII)[d]

| time (min) | solvent A (%) | solvent B (%) |
|---|---|---|
| 0.0 | 75 | 25 |
| 1.0 | 75 | 25 |
| 23.0 | 55 | 45 |
| 23.1 | 0 | 100 |
| 27.0 | 0 | 100 |
| 27.1 | 75 | 25 |
| 30.0 | 75 | 25 |

Media (Adjusted to pH to 7.0 with 50 mM HEPES)

TABLE 6

MD1 (pre-culture medium)[e]

| Substance | Concentration [g/L] |
|---|---|
| Casitone | 3 |
| $CaCl_2 \times 2 H_2O$ | 0.5 |
| $MgSO_4 \times 7 H_2O$ | 2 |
| D(+)-Glucose water free | 1 |
| Cyanocobalamine | 0.5 mg |
| Antifoam B | 0.2 mL |
| Ferrioxamine solution [100 ng/mL] | 1 mL |

TABLE 7

POL1 (production medium)[f]

| Substance | Concentration [g/L] |
|---|---|
| Alburex | 4 |
| Soluble starch | 3 |
| $CaCl_2 \times 2 H_2O$ | 0.5 |
| $MgSO_4 \times 7 H_2O$ | 2 |
| Cyanocobalamine | 0.25 mg |
| HEPES | 12 |
| Standard Trace Element Solution 1901 | 1 mL |
| XAD16 | 35 |

Characterization of Compounds:
Physical Data of Compound of Formula (VIII)

FT-MS (9.4 T APEX-III). Found: 985.5007. Calc. for $C_{49}H_{70}N_8O_{12}$+Na: 985.5005.

$^1$H NMR (600 MHz) $d_6$-DMSO $\delta_H$: 0.74 (6H, d, J=7.0 Hz), 0.85 (3H, d, J=7.0 Hz), 0.88 (3H, d, J=7.0 Hz), 0.89 (6H, d, J=7.0 Hz), 1.18 (3H, d, J=6.7 Hz), 1.32 (1H, m), 1.46 (1H, m), 1.57 (2H, m), 1.72 (3H, m), 1.81 (1H, m), 1.88 (1H, m), 1.98 (1H, m), 2.02 (2H, m), 2.11 (3H, m), 2.42 (1H, m), 2.73 (1H, m), 2.77 (3H, s), 2.87 (1H, m), 3.12 (1H, m), 3.64 (1H, m), 4.23 (1H, m), 4.40 (1H, m), 4.58 (1H, d, J=9.5 Hz), 4.75 (2H, m), 4.93 (1H, m), 5.07 (1H, s), 5.40 (1H, m), 6.03 (1H, s), 6.74 (1H, s), 6.79 (2H, d, J=8.4 Hz), 6.84 (2H, d, J=7.8 Hz), 7.02 (2H, d, J=8.4 Hz), 7.10 (1H, d, J=9.3 Hz), 7.14 (1H, t, J=7.8 Hz), 7.19 (2H, t, J=7.8 Hz), 7.26 (1H, s), 7.42 (1H, d, J=9.8 Hz), 7.89 (1H, d, J=9.2 Hz), 8.03 (1H, d, J=7.9 Hz), 8.38 (1H, d, J=8.9 Hz), 9.40 (1H, s)

$^{13}$C NMR (150 MHz) d$_6$-DMSO $\delta_C$: 17.13, CH$_3$; 17.63, CH$_3$; 19.32, CH$_3$; 20.90, CH$_3$; 21.64, CH$_2$; 22.34, CH$_3$; 22.34, CH$_3$; 23.32, CH$_3$; 24.10, CH; 25.63, CH; 27.63, CH$_2$; 29.30, CH$_2$; 30.37, CH$_3$; 30.86, CH; 31.52, CH$_2$; 32.83, CH$_2$; 35.33, CH$_2$; 38.98, CH$_2$; 44.42, CH$_2$; 48.52, CH; 50.19, CH; 50.24, CH; 51.99, CH; 54.62, CH; 55.63, CH; 60.90, CH; 71.86 CH; 73.70, CH; 115.32, 2×CH; 126.21, CH; 127.50, Cq; 127.74, 2×CH; 129.42, 2×CH; 130.43, 2×CH; 136.72, Cq; 156.23, Cq; 168.93, Cq; 169.18, Cq; 169.18, Cq; 170.18, Cq; 170.39, Cq; 171.72, Cq; 171.96, Cq; 172.50, Cq; 173.82, Cq Physical Data of Compound of Formula (IX)

FT-MS (9.4 T APEX-III). Found: 969.5058. Calc. for C$_{49}$H$_{70}$N$_8$O$_{11}$+Na; 969.5056.

$^1$H NMR (600 MHz) d$_6$-DMSO $\delta_H$): 0.53 (3H, d, J=6.6 Hz), 0.73 (3H, d, J=6.6 Hz), 0.74 (3H, d, J=6.6 Hz), 0.81 (3H, d, J=6.6 Hz), 0.86 (6H, d, J=6.6 Hz), 1.08 (3H, d, J=6.5 Hz), 1.20 (1H, m), 1.33 (3H, m), 1.52 (1H, m), 1.64 (1H, m), 1.80 (2H, m), 2.01 (1H, m), 2.04 (2H, m), 2.15 (4H, m), 2.25 (1H, m), 2.30 (1H, m), 2.74 (3H, s), 2.83 (1H, m), 3.12 (1H, m), 3.32 (1H, m), 3.38 (1H, m), 4.14 (1H, m), 4.27 (1H, m), 4.40 (1H, m), 4.59 (1H, m), 4.61 (1H, m), 4.94 (1H, m), 4.99 (1H, m), 5.10 (1H, m), 6.42 (2H, d, J=8.8 Hz), 6.75 (1H, s), 7.04 (2H, d, J=8.8 Hz), 7.10 (1H, t, J=7.3 Hz), 7.15 (2H, t, J=7.3 Hz), 7.23 (2H, d, J=7.3 Hz), 7.30 (1H, s), 7.41 (1H, d, J=9.5 Hz), 8.05 (1H, d, J=9.5 Hz), 8.23 (1H, d, J=8.1 Hz), 8.47 (1H, d, J=4.4 Hz), 8.71 (1H, d, J=10.2 Hz). (signal of proton of hydroxy group of tyrosine not visible)

Physical Data of Compound of Formula (X)

FT-MS (9.4 T APEX-III). Found: 955.4896. Calc. for C$_{48}$H$_{68}$N$_8$O$_{11}$+Na: 955.4900.

$^1$H NMR (600 MHz) d$_6$-DMSO $\delta_H$). O$_H$: no assignment of chemical shifts (mixture of rotameres, assignment of structure based on comparison of NMR data (missing N-methyl-group) with NMR data of compound (IX).

Example 3

Biological Activity

The compounds of the present invention, e.g. including a compound of formula II-X, exhibit pharmacological activity and are therefore useful as pharmaceuticals. E.g., the compounds of the present invention are found to inhibit Kallikrein-7 activity.

Compounds of the present invention have IC$_{50}$ values between 1 nM and 10 µM as determined in the following assay:

Materials and Buffers

The fluorescence-quenched substrate Ac-Glu-Asp (EDANS)-Lys-Pro-Ile-Leu-Phe^Arg-Leu-Gly-Lys(DAB-CYL)-Glu-NH$_2$ (SEQ ID NO1) (where ^ indicates the scissile bond, identified by MS analysis) is purchased from Biosyntan (Berlin, Germany) and kept as a 5 mM stock solution in DMSO at −20° C. All other chemicals are of analytical grade.

Enzymatic reactions are conducted in 50 mM sodium citrate buffer at pH 5.6 containing 150 mM NaCl and 0.05% (w/v) CHAPS.

All protein and peptide containing solutions are handled in siliconized tubes (Life Systems Design, Merenschwand, Switzerland). The compound solutions as well as the enzyme and the substrate solutions are transferred to the 384-well plates (black Cliniplate; cat. no. 95040020 Labsystems Oy, Finland) by means of a CyBi-Well 96-channel pipettor (Cy-Bio AG, Jena, Germany).

Instrumentation for FI Measurements

For fluorescence intensity (FI) measurements an Ultra Evolution reader (TECAN, Maennedorf, Switzerland) is used. The instrument is equipped with a combination of a 350 nm (20 nm bandwidth) and a 500 nm (25 nm bandwidth) bandpath filter for fluorescence excitation and emission acquisition, respectively. To increase the signal:background ratio, an appropriate dichroic mirror is employed. The optical filters and the dichroic mirror are purchased from TECAN. The fluorophores in each well are excited by three flashes per measurement.

Determination of IC$_{50}$ Values

For the determination of IC$_{50}$ values the assay is performed at room temperature in 384-well plates. All final assay volumes were 30 µl. Test compounds are dissolved in 90% (v/v) DMSO/water and diluted in water (containing 0.05% (w/v) CHAPS) to 3-times the desired assay concentration. The 11 final compound concentrations are: 0.3 nM, 1 nM, 3 nM, 10 nM, 30 nM, 100 nM, 300 nM, 1 µM, 3 µM, 10 µM and 30 µM. For each assay, 10 µl water/CHAPS (±test compound) are added per well, followed by 10 µl protease solution (diluted with 1.5× assay buffer). The protease concentration in final assay solution is 0.2 nM (according to the enzyme concentrations determined by the Bradford method). After 1 hour of incubation at room temperature, the reaction is started by addition of 10 µl substrate solution (substrate dissolved in 1.5× assay buffer, final concentration was 2 µM). The effect of the compound on the enzymatic activity is obtained from the linear progress curves and determined from two readings, the first one taken directly after the addition of substrate and the second one after 1 hour. The IC$_{50}$ value is calculated from the plot of percentage of inhibition vs. inhibitor concentration using non-linear regression analysis software (XLfit, Vers. 4.0; ID Business Solution Ltd., Guildford, Surrey, UK).

TABLE 8

| Enzyme | Cyclic depsipeptide according to formula (II) IC50 µM | Cyclic depsipeptide according to formula (III) IC50 µM | Cyclic depsipeptide according to formula (IV) IC50 µM | Cyclic depsipeptide according to formula (V) IC50 µM |
|---|---|---|---|---|
| hKallikrein7 | 0.001 | 0.0004 | 0.005 | 0.006 |

In addition, the cyclic depsipeptides inhibited human chymotrypsin and human neutrophile elastase with an IC50 ranging from 0.001 µM to 0.02 µM and from 0.01 µM to 0.07 µM, respectively.

The biological activity of the cyclic depsipeptide according to formula (VIII) was determined with kallikrein 7. This cyclic depsipeptide of the invention inhibits human kallikrein 7 with an IC$_{50}$ of less than 3 nM. This cyclic depsipeptide inhibited human chymotrypsin and human neutrophile elastase with an IC50 around 0.004 OA and around 0.0025 µM, respectively.

Example 4

Derivatisation of a Cyclic Depsipeptide of the Invention

To a solution of 20 mg of cyclic depsipeptide according to formula (II) and 0.027 mL triethylsilane in 2 mL of dichloromethane/acetonitrile (1:1) at −50° C. 0.014 mL of boron trifluoride etherate were slowly added. The reaction mixture was allowed to warm up to −5° C. and kept at this temperature for additional 30 minutes, poured into a saturated NaHCO$_3$ solution, and was extracted with ethyl acetate. The organic layer was dried over sodium sulfate and the solvent was removed in vacuo. Purification of the residue obtained by HPLC (XTerra [5 cm]; acetonitrile/ammonium carbonate buffer pH10 gradient) provided 9.8 mg of a derivative of the cyclic depsipeptide according to formula (II) wherein the Ahp has been converted into 3-amino-2-piperidone.

Example 5

Derivatisation of a Cyclic Depsipeptide of the Invention

To a solution of 75 mg (0.081 mmol) of cyclic depsipeptide according to formula (II) in 5 mL of 1-PrOH 30 μL of sulfuric acid were added and the reaction mixture was stirred for 48 hours at rt. For workup the reaction mixture was diluted with methylene chloride and washed with sat. bicarbonate solution. After drying of the organic layer over sodium sulfate the solvent was removed and the residue obtained purified by chromatography on silica gel (cHex/EtOAc (1:1)+10% MeOH). Yield: 65 mg (83%) of a derivative of the cyclic depsipeptide according to formula (II) wherein the Ahp has been converted into a 1-propyl-ketal-Ahp.

Example 6

Derivatisation of a Cyclic Depsipeptide of the Invention

To a solution of 75 mg (0.081 mmol) of cyclic depsipeptide according to formula (II) in 5 mL of 1-OctylOH 30 μL of sulfuric acid were added and the reaction mixture was stirred for 48 hours at rt. For workup the reaction mixture was diluted with methylene chloride and washed with sat. bicarbonate solution. After drying of the organic layer over sodium sulfate the solvent was removed and the residue obtained purified by chromatography on silica gel (cHex/EtOAc (1:1)+10% MeOH). Yield: 52 mg (62%) of a derivative of the cyclic depsipeptide according to formula (II) wherein the Ahp has been converted into a 1-octyl-ketal-Ahp.

Example 7

Derivatisation of a Cyclic Depsipeptide of the Invention

A solution of 25 mg (0.027 mmol) of cyclic depsipeptide according to formula (II) in 2 mL of dichloromethane (MC) was cooled to 0° C. Then DIEA and trifluoroacetic acid anhydride (TFAA) was added. The reaction mixture was slowly warmed up to room temperature and stirred for additional 4 hours. For workup the reaction mixture was diluted with MC and washed with hydrochloric acid and sat. bicarbonate solution. After drying over sodium sulfate the solvent was removed and the residue obtained purified by chromatography on silica gel (cHex/EtOAc (1:1)+10% MeOH). Yield: 14 mg (57%) of a derivative of the cyclic depsipeptide according to formula (II) wherein the amide of A1 has been converted into a nitrile.

Example 8

Derivatisation of a Cyclic Depsipeptide of the Invention

To a solution of 1 g of cyclic depsipeptide according to formula (II) in 300 mL of dichloromethane/acetonitrile (1:1) at −50° C. 0.68 mL of boron trifluoride etherate were slowly added. The reaction mixture was allowed to warm up to −20° C. Then additional 0.68 mL of boron trifluoride etherate were slowly added the reaction mixture kept at this temperature until no more starting material could be observed (HPLC). Then the reaction mixture was poured into a saturated NaHCO$_3$ solution, and was extracted with ethyl acetate. The organic layer was dried over sodium sulfate and the solvent was removed in vacuo providing a derivative of the cyclic depsipeptide according to formula (II) wherein the Ahp has been converted into 3-amino-3,4-dihydro-1H-pyridin-2-on.

The crude material was dissolved in 400 mL of 2-propanol, 115 mg of Pd/C (10%) were added and the mixture was hydrogenated under atmospheric pressure until the starting material was consumed (HPLC). The residue obtained was purified by chromatography (SiO$_2$; cHex/EtOAc (1:1)+10% MeOH) providing 684 mg of the cyclic depsipeptide according to formula (II) wherein the Ahp has been converted into 3-amino-2-piperidone.

REFERENCES

[Bode H B, Zeggel B, Silakowski B, Wenzel S C, Reichenbach H, Müller R (2003)] Steroid biosynthesis in prokaryotes: identification of myxobacterial steroids and cloning of the first bacterial 2,3(S)-oxidosqualene cyclase from the myxobacterium *Stigmatella aurantiaca*. Mol Microbiol 47:471-481

[Das S K, Mishra A K, Tindall B J, Rainey F A, Stackebrandt E (1996)] Oxidation of thiosulfate by a new bacterium, *Bosea thiooxidans* (strain BI-42) gen. nov., sp. nov.: Analysis of phylogeny based on chemotaxonomy and 16S ribosomal DNA sequencing. Int J Syst Bacteriol 46:981-987

[Dictionary of Natural Products (2007)] Dictionary of Natural products on CD-ROM, version 15.2, 2007, Hampen Data services Ltd.

[DSMZ (2007)] Description of biological risk group of *Chondromyces* strains [Gerth K, Pradell A, Perlova O, et al. (2003)] Myxobacteria: proficient producers of novel natural products with various biological activities—past and future biotechnological aspects with the focus on the genus *Sorangium*. J Biotechnol 106:233-253.

[Hansson L, Backman A, Ny A, Edlund M, Ekholm E, Ekstrand Hammarstrom B, Tornell J, Wallbrandt P, Wennbo H, Egelrud T (2002)] Epidermal overexpression of stratum corneum chymotryptic enzyme in mice: a model for chronic itchy dermatitis. J Invest Dermatol 118:444-449

[Ishida K, Matsuda H, Murakami M, Yamaguchi K (1996)] The Absolute Stereochemistry of micropeptin 90. Tetrahedron letters 37:51-52.

[Jacobi C A, Reichenback H, Tindall B J, Stackebrandt E (1996)] "Candidatus comitans," a bacterium living in coculture with Chondromyces crocatus (Myxobacteria). Int J Syst Bacteriol 46:119-122

[Jacobi C A, Assmus B, Reichenbach H, Stackebrandt E (1997)] Molecular evidence for association between the Sphingobacterium-like organism "Candidatus comitans" and the myxobacterium Chondromyces crocatus. Appl Environ Microbiol 63:719-723

[Jansen R, Kunse B, Reichenbach H, Höfle G (2002)] The ajudazols A and B, novel isochromanones from Chondromyces crocatus (Myxobacteria): Isolation and structure elucidation. Eur J Org Chem 2002:917-921

[Kaiser D (2003)] Coupling cell movement to multicellular development in myxobacteria. Nature Reviews Micobiol 1:45-54

[Kunze B, Jansen R, Sasse F, et al. (1995)] Chondramides A~D, new antifungal and cytostatic depsipeptides from Chondromyces crocatus (Myxobacteria): Production, physicochemical and biological properties. J Antibiotics 48:1262-1266

[La Scola B, Mallet M-N, Grimont PAD, Raoult D (2003)] Bosea eneae sp. nov., Bosea massiliensis sp. nov. and Bosea vestrisii sp. nov., isolated from hospital water supplies, and emendation of the genus Bosea (Das et al. 1996). Int J Syst Evol Microbiol 53:15-20

[Lee A Y, Smitka T A, Bonjouklian R, Clardy J (1994)] Atomic structure of the trypsin-A90720A complex: a unified approach to structure and function. Chemistry & Biology 1:113-117

[Matern U, Schleberger C, Jelakovic S, Weckesser J, Schulz G E (2003)] Binding structure of elastase inhibitor scyptolin A. Chemistry & Biology 10:997-1001

[Rahid S, et al. (2006)] Molecular and biochemical studies of chondramide formation—highly cytotoxic natural products from Chondromyces crocatus Cm c5. Chem & Biol 14:667-681

[Rouhiainen L, Paulin L, Suomalainen S, Hyytiäinen H, Buikema W, Haselkorn R, Sivonen K (2000)] Genes encoding for synthetases of cyclic depsipetides, anabaenopeptilides, in Anabaena strain 90. Molecular Microbiology 37:156-167.

[Vasilopoulos Y, Cork M J, Murphy R, et al. (2004)] Genetic association between an AACC insertion in the 3'UTR of the stratum corneum chymotryptic enzyme gene and atopic dermatitis. J Invest Dermatol 123:62-66

The invention claimed is:

1. Method of treating a subject suffering from a kallikrein 7-dependent disease selected from Netherton's syndrome, pruritic dermatoses and psoriasis, comprising: administering to said subject a therapeutically effective amount of a cyclic depsipeptide, having the structure of formula (I):

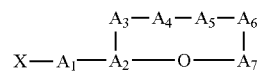

wherein the ester bond is found between the carboxy group of A7 and the hydroxy group of A2,
wherein X and $A_1$ are each independently optional,
and wherein
X is chemical residue selected from substituted or unsubstituted aliphatic group, substituted or unsubstituted aryl, substituted or unsubstituted arylalkyl, substituted or unsubstituted heteroaryl, or halogen,
$A_1$ is a standard amino acid,
$A_2$ is threonine or serine or 5-methylhydroxyproline,
$A_3$ is a non-basic standard amino acid or a non-basic non-standard amino acid selected from selenocysteine, pyrrolvsine, lanthionine, 2-aminoisobutyric acid, dehydroalanine, 3-amino-6-hydroxy-2-piperidone, gamma-aminobutyric acid, homocysteine, dopamine or hydroxyproline, or a non-basic standard amino acid derivative,
$A_4$ is Ahp, dehydro-AHP, proline or a derivative thereof selected from 3-amino-2-piperidone and ether and ester derivatives of AHP,
$A_5$ is isoleucine, leucine, phenylalanin, prolin, threonine, or valine,
$A_6$ is alanine, phenylalanine, tryptophan, tyrosine or a tyrosine derivative thereof
$A_7$ is leucine, isoleucine or valine,
wherein the nitrogen atom of the amid bond between A5 and A6 can be substituted with a methyl or a pharmaceutically acceptable salt of cyclic depsipeptide.

2. The method of claim 1 wherein X is H or an acyl residue.

3. The method of claim 1 wherein X is $CH_3CH_2CH(CH_3)CO$, $(CH_3)_2CHCH_2CO$ or $(CH_3)_2CHCO$.

4. The method of treating a subject suffering from Netherton's syndrome, pruritic dermatoses, prurigo nodularis or pustular psoriasis according to claim 2.

5. The method of treating a subject suffering from Netherton's syndrome, pruritic dermatoses, prurigo nodularis or pustular psoriasis according to claim 3.

6. The method of claim 1 wherein the kallikrein 7-dependent disease is prurigo nodularis or pustular psoriasis.

7. The method of claim 2 wherein the kallikrein 7-dependent disease is prurigo nodularis or pustular psoriasis.

8. The method of claim 3 wherein the kallikrein 7-dependent disease is prurigo nodularis or pustular psoriasis.

\* \* \* \* \*